United States Patent [19]
Taylor et al.

[11] Patent Number: 5,913,819
[45] Date of Patent: Jun. 22, 1999

[54] INJECTION MOLDED, HEAT-SEALED HOUSING AND HALF-ETCHED LEAD FRAME FOR OXIMETER SENSOR

[75] Inventors: James H. Taylor, Broomfield; Daniel A. Estoque, Boulder; Kirk L. Weimer, Superior, all of Colo.

[73] Assignee: Datex-Ohmeda, Inc., Louisville, Colo.

[21] Appl. No.: 08/826,698

[22] Filed: Apr. 7, 1997

Related U.S. Application Data

[60] Provisional application No. 60/016,356, Apr. 26, 1996.

[51] Int. Cl.$^6$ .................... H61B 5/00; H05K 3/30
[52] U.S. Cl. .................... 600/323; 29/832; 29/847
[58] Field of Search .................... 600/310, 322, 600/323, 340, 344; 29/832, 846, 847, 848

[56] References Cited

U.S. PATENT DOCUMENTS

| | | | |
|---|---|---|---|
| 4,876,587 | 10/1989 | Hilton et al. | 357/70 |
| 5,170,786 | 12/1992 | Thomas et al. | 128/633 |
| 5,237,994 | 8/1993 | Goldberger | 600/323 |
| 5,263,244 | 11/1993 | Centa et al. | 600/323 |
| 5,425,360 | 6/1995 | Nelson | 600/323 |

FOREIGN PATENT DOCUMENTS

| | | |
|---|---|---|
| 0 104 772 A2 | 4/1984 | European Pat. Off. . |
| 0 127 947 A2 | 12/1984 | European Pat. Off. . |
| 0 538 631 A1 | 4/1993 | European Pat. Off. . |
| 3809084 A1 | 9/1989 | Germany . |
| WO 92/21280 | 12/1992 | WIPO . |
| WO 94/12096 | 6/1994 | WIPO . |

*Primary Examiner*—Cary O'Connor
*Assistant Examiner*—Eric F. Winakur
*Attorney, Agent, or Firm*—Holme Roberts & Owen LLP

[57] ABSTRACT

The present invention is directed to an oximeter sensor to measure the oxygen content of a patient's blood. The sensor can include a lead frame having different thicknesses, a sensor housing being molded from a common thermoplastic resin, and rib members in the housing for inhibiting shorting between adjacent traces of the lead frame. The present invention further includes a process for forming the sensor.

44 Claims, 29 Drawing Sheets

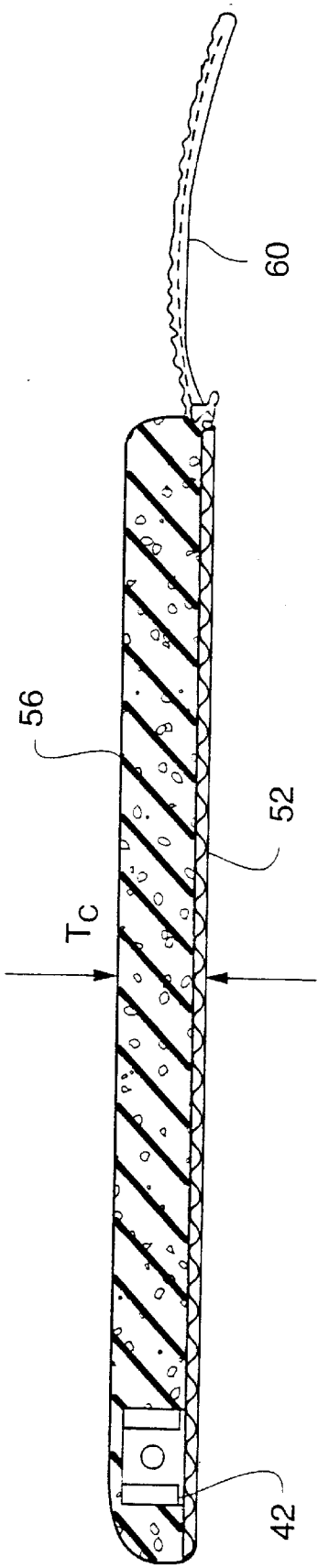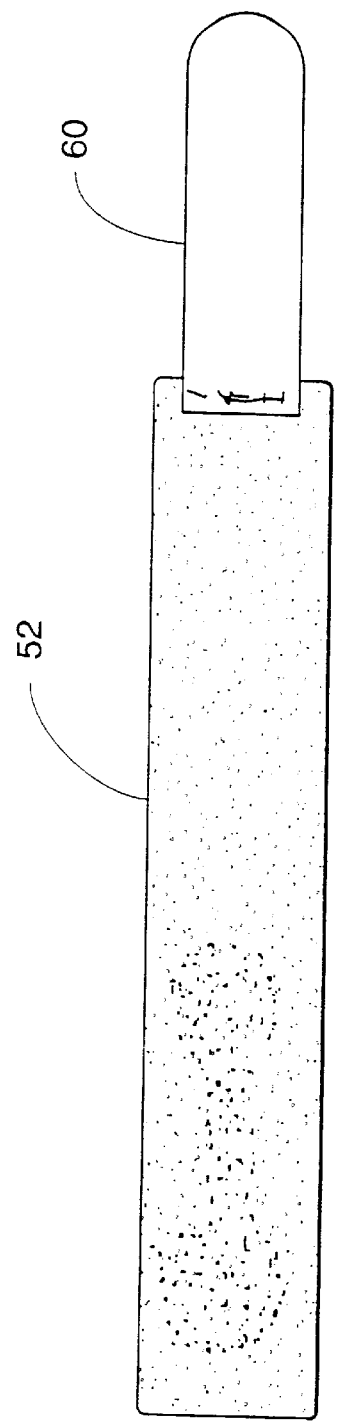
Fig. 3
Fig. 4

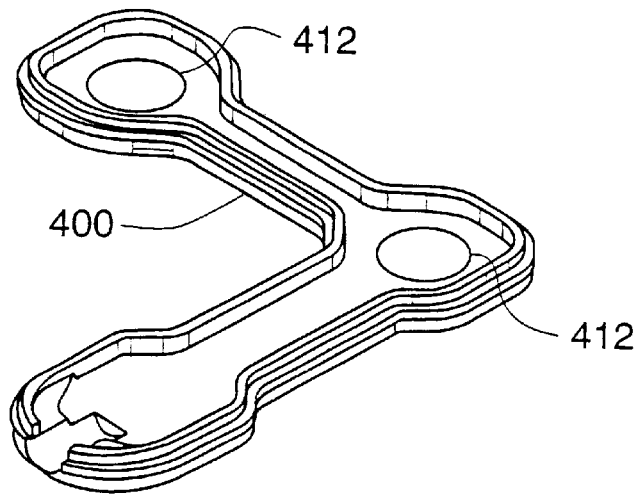
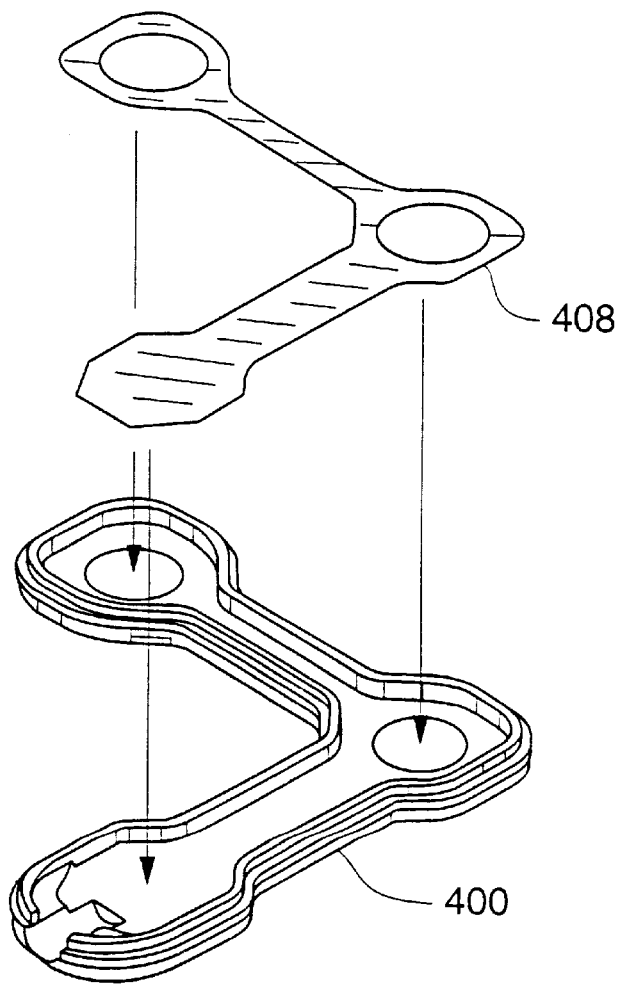
Fig. 22

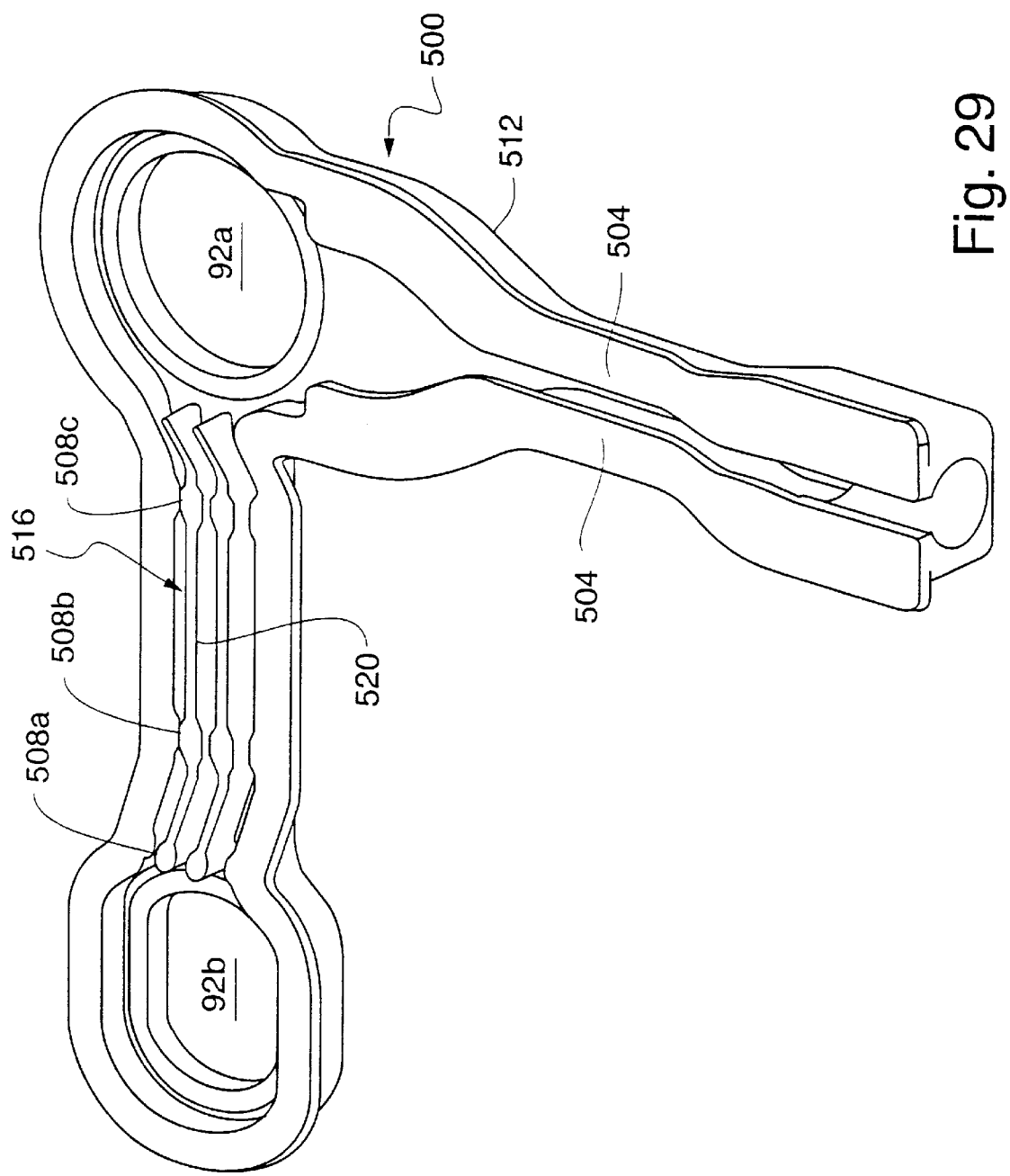

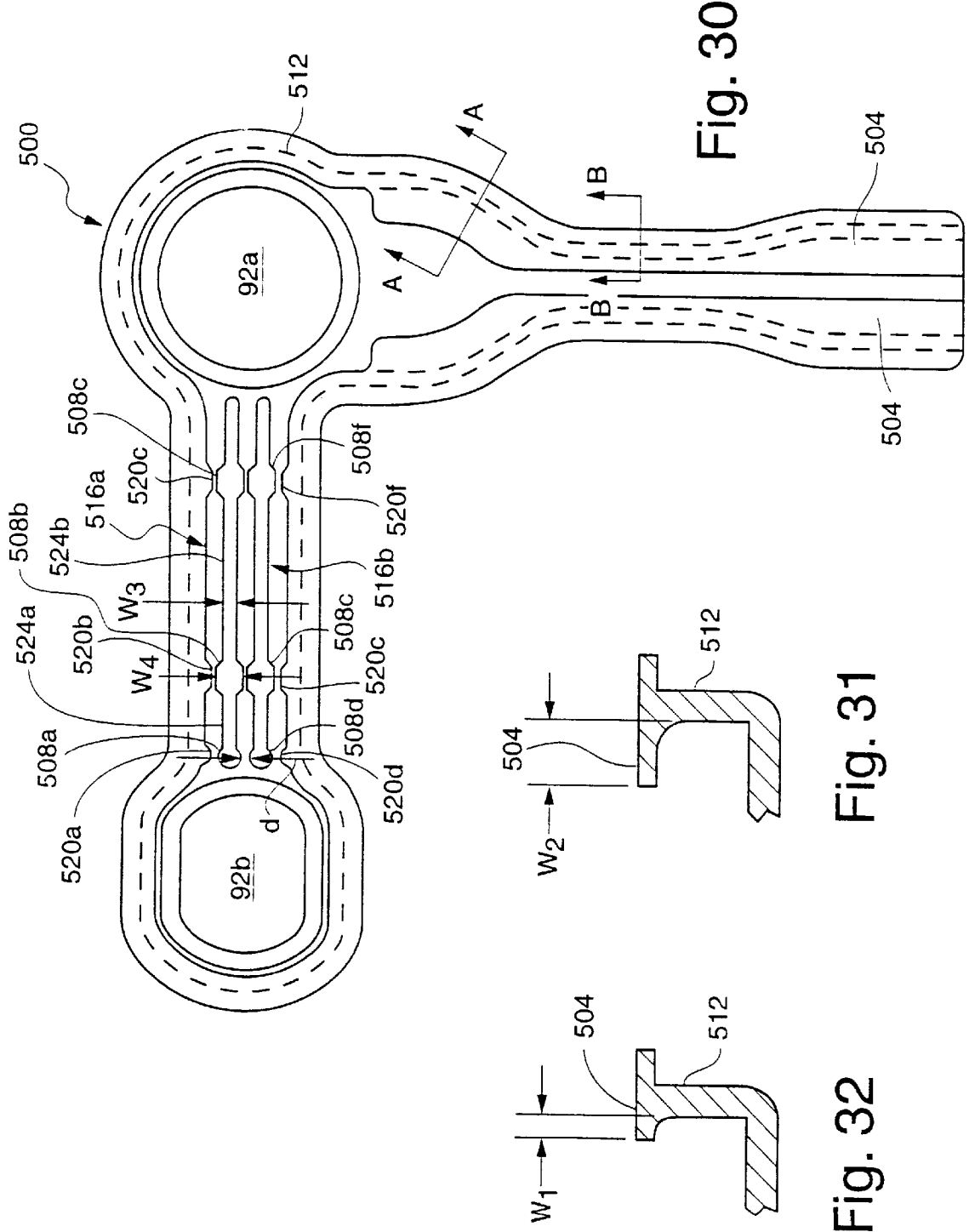

INJECTION MOLDED, HEAT-SEALED HOUSING AND HALF-ETCHED LEAD FRAME FOR OXIMETER SENSOR

The present application claims priority from U.S. Provisional Application Ser. No. 60/016,356 entitled "Conformal Wrap for Oximeter Sensor", filed Apr. 26, 1996, which is incorporated herein by reference in its entirety.

FIELD OF THE INVENTION

The present invention is generally directed to photoplethysmographic measurement instruments and specifically to housings and lead frames for oximeter sensors.

BACKGROUND OF THE INVENTION

A common method used to identify problems with a patient's respiratory system is pulse oximetry. The color of the blood (i.e., the amounts of red and infrared radiation absorbed by the blood) is a function of the oxygen saturation of the heme in the blood's hemoglobin. For example, heme that is saturated with oxygen appears bright red because saturated heme is highly permeable to red light. In contrast, heme that is deoxygenated appears dark and bluish as it is less permeable to red light. A pulse oximeter measures the oxygen content of arterial blood by irradiating the blood with red and infrared radiation and determining the corresponding amounts of the red and infrared radiation that are absorbed by the heme in the blood.

A pulse oximeter sensor generally includes one or more emitters, a leadframe and a detector, all of which are located within a light impermeable housing. The leadframe, which is formed by a number of discrete conductive strips (also called traces), is used to electrically connect the emitters and detector with a pulse oximeter processing and display unit. The oximeter processing and display unit sequentially energizes the emitters and analyzes the resulting signals received from the detector to determine the oxygen content of the patient's blood.

There are a number of competing design objectives for pulse oximeter sensors. First, the lead frame must be thin enough to be flexible to conform to the body part to which it is attached, yet thick enough to conduct heat away from electrical parts, such as the LEDs and detector. Second, many applications, particularly when using the oximeter sensor with patients having sensitive skin such as premature infants and burn victims, it is desirable to have a relatively soft patient/sensor interface. Third, to protect the detector, LEDs and other electrical components from the terrestrial environment, it is important to have a seal between the light transparent lenses covering the LEDs and detector on the one hand and the light opaque sensor housing on the other that has a high degree of integrity. Fourth, the transition between the lens and the surrounding portions of the sensor body should also be relatively smooth to inhibit skin abrasion. Finally, it is desirable to have an oximeter sensor that is configured for ease of assembly. For example, it is desirable to have an oximeter sensor body that does not require an overmolding step during fabrication. Overmolding is an expensive process that requires high cost tooling and a molding machine. If the sensor manufacturer does not have a molding machine available, the various sensor components are typically shipped back to the molder for final assembly.

SUMMARY OF THE INVENTION

It is an objective of the present invention to provide an oximeter sensor that is inexpensive and/or disposable after one or a few applications. A related objective is to provide an oximeter sensor configured for ease of assembly and/or elimination of the overmolding step during assembly of the sensor body.

Another objective of the present invention is to provide an oximeter sensor that has a seal between the lenses and the sensor body that has a high degree of integrity.

Yet another objective of the present invention is to provide a lead frame that is thin enough to be flexible, yet thick enough to conduct heat away from electrical parts, such as the detector and LEDs.

These and other objectives are addressed by the pulse oximeter sensor of the present invention. The invention provides a sensing device for measuring the oxygen content of a patient's bloodstream. The sensing device includes a housing for containing at least one of (a) an emitter means for irradiating the patient's bloodstream and (b) a detector means for providing a signal and response to a radiation portion passing through the bloodstream. The housing includes one or more substantially transparent lenses adjacent to the emitter means and/or detector means to pass radiation and an opaque housing body enclosing the emitter means and/or detector means. The lenses are substantially free of light absorptive components such as color bodies (e.g., pigments), while the housing body has a significant amount of light absorptive components. The housing body and lenses are formed from one or more common polymers. The lenses and housing can thus be formed from a common intermediate thermoplastic resin formed from the polymers. The resin is substantially light transparent. The use of such a resin for both the lenses and housing body not only provides a more comfortable patient interface due to a relatively smooth transition between the lenses and the housing body but also simplifies assembly of the sensor.

Although a common intermediate thermoplastic resin is employed for the lenses and housing body, a number of additives, such as light absorptive or reflective color bodies, are typically added to the thermoplastic resin portion used for the housing body. In contrast, the portion of the resin used for the lenses is substantially free of additives such as color bodies. Generally, the portion of the resin used for the housing body contains from about 2 to about 30% by weight color bodies.

Because the same thermoplastic resin is used for the lenses and housing body, the lenses and housing body have a number of similar properties. By way of example, the lenses and housing body typically have substantially the same melting point, yield and ultimate tensile strengths, moduli of elasticity, coefficients of thermal expansion and contraction, and durometer. The similar properties prevent separation of the lenses from the housing body due to stress induced by external forces or thermal expansion/contraction cycles.

The housing body can have a plurality of rib members to inhibit shorting between electrical traces in the lead frame. One or more of the rib members are received between adjacent traces of the lead frame. In one application, a first set of traces is located between the detector means and the emitter means and a second set of traces is located between the detector means and/or emitter means and wire means for connecting the sensing device to the oximeter processing and display unit. A first set of rib members engages the first set of traces, and a second set of rib members engages the second set of traces.

To facilitate ease of assembly and eliminate the need for an overmolding step, the housing can have upper and lower portions each having a lip projecting outwardly from the portion. The lip portion of the upper portion is sealed to the lip portion of the lower portion to protect the emitter means and/or detector means from fluids in the terrestrial environment.

The lead frame can have a first portion having a first thickness and a second portion having a second thickness. The first thickness is greater than the second thickness. The first portion generally contacts at least one of the detector means and emitter means to conduct heat away from the components. The second portion is typically located in the central area of the leadframe, (i.e., between the detector means and emitter means, which are located at opposite ends of the lead frame) to provide flexibility of the sensing device and permit it to be readily bent to conform to a body part, such as a finger. As will be appreciated, the detector means and emitter means are in an opposing relationship when the oxygen saturation measurement is made. In one application, the lead frame includes a first set of traces between the emitter means and detector means and a second set of traces extending from at least one of the emitter means and detector means to the wire means. The first portion includes the second set of traces and the second portion includes the first set of traces.

To provide ease of assembly, the first and second portions of the lead frame can be simultaneously cut from a common conductive sheet, typically using a common die. The lead frame can then be selectively etched to provide first and second portions having different thickness.

The present invention further provides a method for forming an oximeter sensing device. The method includes the steps:

(a) forming the intermediate thermoplastic resin;

(b) molding a first portion of the intermediate thermoplastic resin to form a substantially light transparent lens for at least one of a detector and emitter;

(c) mixing a second portion of the intermediate thermoplastic resin with a color body to form a color-body containing thermoplastic resin; and (d) molding the color-body containing thermoplastic resin to form a substantially opaque housing body for the oximeter sensing device.

Where lips are included on upper and lower portions of the housing to facilitate assembly of the housing, the method can include the steps of engaging a first lip on the upper portion of the housing with a second lip on a lower portion of the housing and heating the upper and lower portions to above the melting point of the thermoplastic resin to seal the upper portion to the lower portion.

The present invention further includes a method for forming a lead frame for the oximeter sensor. The method includes the step of cutting the lead frame from a conductive sheet using a mask or cutting die having substantially the same size and shape as a cavity in the sensor housing for receiving the lead frame.

In some applications, the method can include the step of applying an etchant to a selected portion of the lead frame body to form a lead frame having different thicknesses. The applying step can include the substeps of applying a masking material to a second portion of the lead frame body other than the selected portion and applying the etchant to the selected portion and the second portion. In other applications, the applying step can include the steps of etching the selected portion of the lead frame body for a first time period and etching another portion of the lead frame for a second time period, with the first time period exceeding the second time period.

The sensing device can be inexpensive and therefore disposed of after one or a few applications. In this regard, the sensing device is preferably composed of relatively inexpensive materials and, due to the assembly's small number of component parts, is simple to manufacture. The sensing device is thus preferable to existing sensors which are composed of relatively expensive materials, have a large number of component parts, and/or are expensive to manufacture.

BRIEF DESCRIPTION OF THE DRAWINGS

FIG. 3 is a side view of the sensing device;

FIG. 4 is a bottom view of the sensing device showing the backing material;

FIGS. 21–24 depict another alternative embodiment of the sensing device of the present invention;

FIGS. 29–32 depict another embodiment of the housing body with FIG. 31 being a cross-section along line A—A and FIG. 32 a cross-section along line B—B.

DETAILED DESCRIPTION

Figure 1:
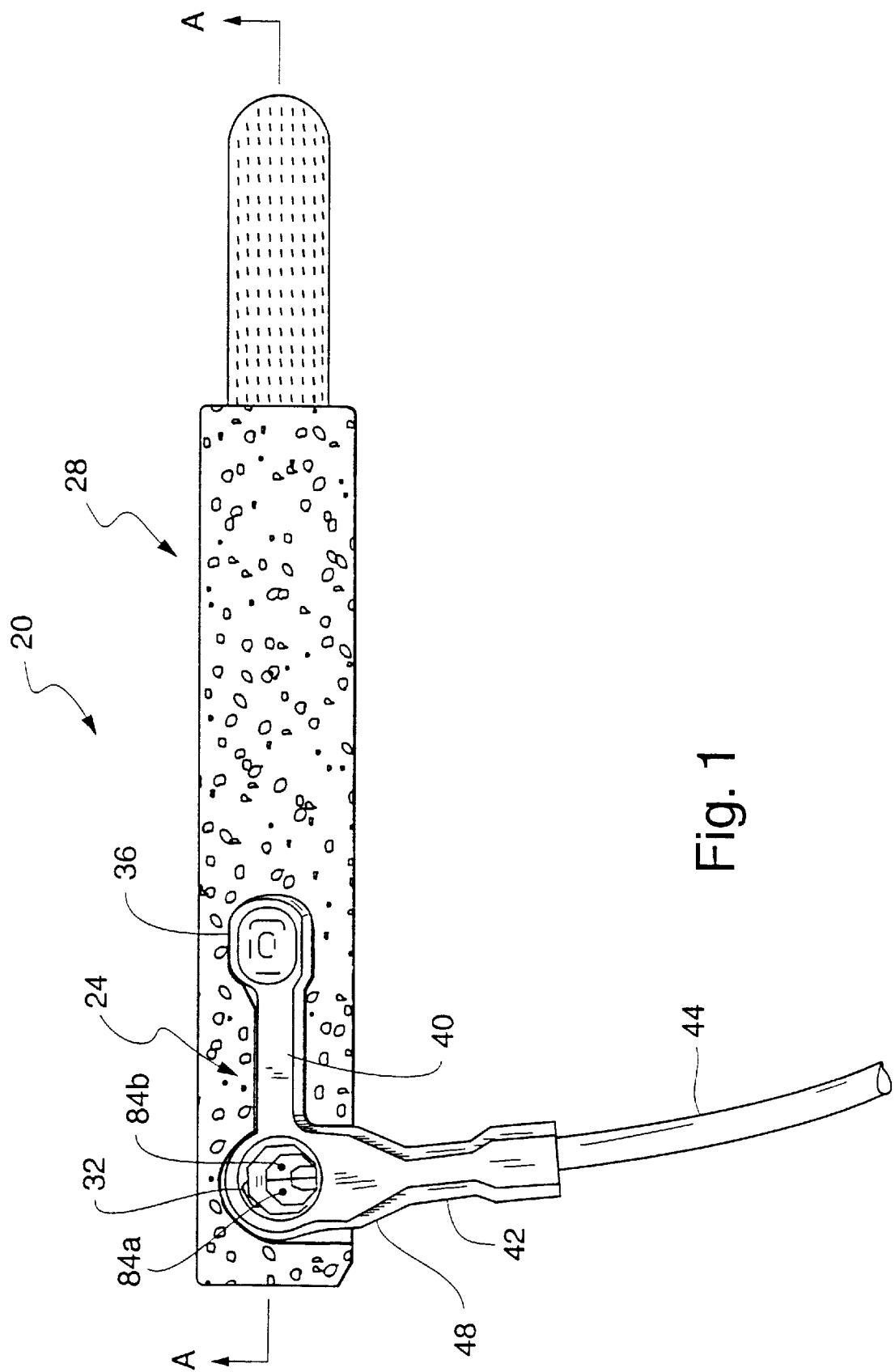
FIGS. 1 and 2 are plan views of a sensing device according to the present invention with and without the sensing means, respectively.
Figure 2:
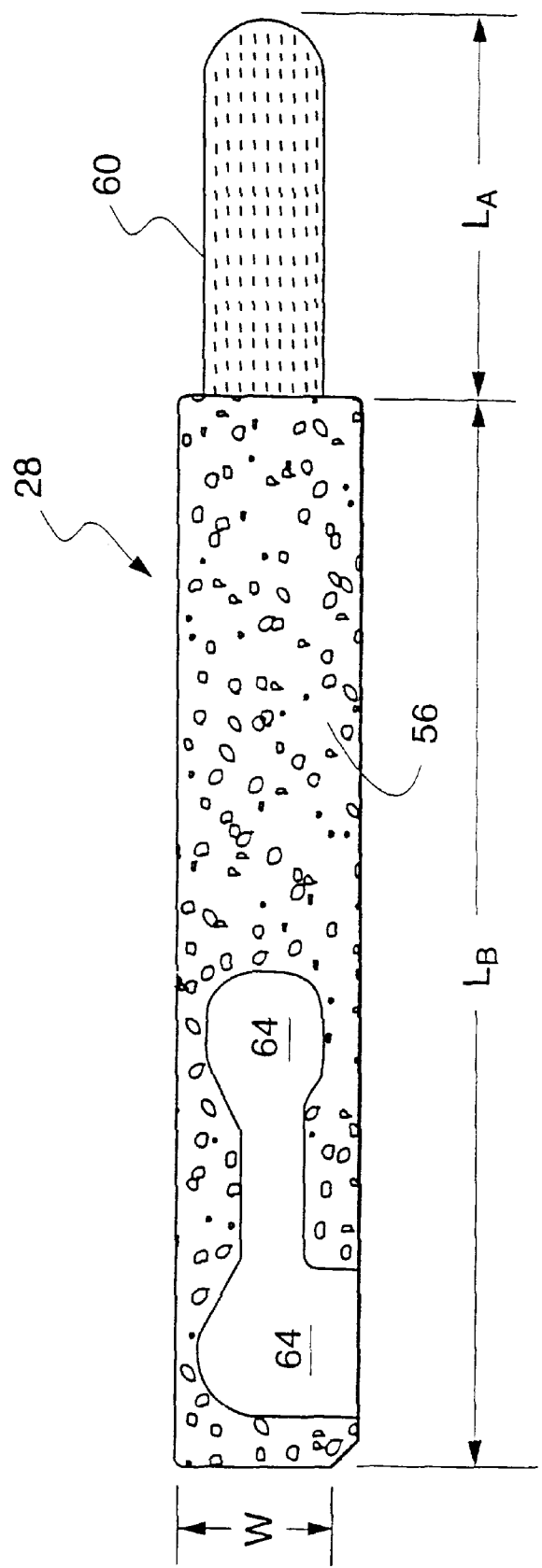
Figure 5:
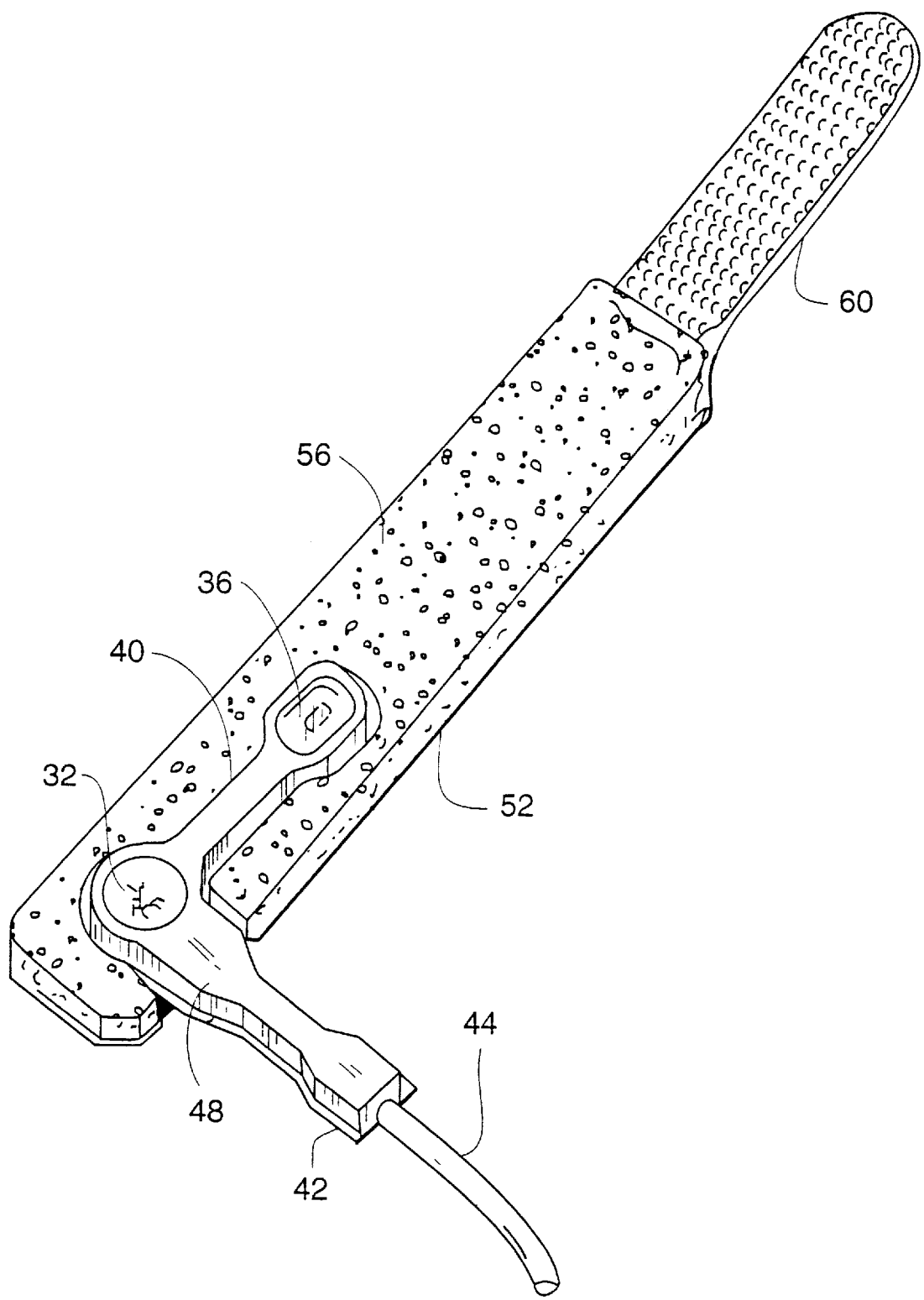
FIG. 5 is a perspective view of the sensing device.

Referring to FIGS. 1–6, a sensing device 20 according to the present invention includes a pulse oximeter sensor 24 for measuring the oxygen content of a patient's blood and a flexible carrier 28 for non-adhesively engaging the patient's skin at the location of the blood oxygen content measurement. The sensor 24 includes an emitter assembly 32 (of one or more emitters) for providing a spectral content, a detector 36 for detecting unabsorbed radiation, and electrical circuitry such as conductive lead 44 for communicating measurement information to a pulse oximeter processing and display unit (not shown), all contained within a substantially light impermeable housing 48. The flexible carrier 28 includes a backing material 52 for imparting strength to the flexible carrier, a compressible material 56 for providing a gentle interface for the patient's skin, and an attachment strap 60 for forming the carrier 28 into a loop for engaging a patient's body part, such as an infant's foot, hand, wrist or ankle. The sensing device 20 attaches to the body part without adhesive or suctional forces between the sensing device and the patient's skin.

The sensor 24 is recessed in a cavity 64 having substantially the same size and shape as the sensor 24 to permit the front surface 68 of the sensor to be substantially level with the upper surface 72 of the compressible material 56. The sensor front surface 68 and front surface 72 of the compressible material are substantially level with few, if any (and preferably no), raised areas to provide a continuous surface contacting the patient's skin. That is, the height "$H_C$" of the front surface 72 above the front surface 76 of the backing material, which typically ranges from about 0.4 to about 1.5 cm, is no less than the height "$H_S$" of the front surface 68 above the front surface 76 of the backing material. In this manner, the sensor front surface and front surface of the compressible material apply to the patient a uniform pressure substantially uniformly across the area of the surfaces and avoids pressure points (i.e., points of elevated pressures relative to surrounding areas). The cavity 64 is typically formed by removing a portion of the compressible material using a cutting die having the same size and shape as the sensor.

To adequately shield the perimeter edges 80 of the sensor from contacting the patient's skin and forming a pressure point, a substantial portion of the perimeter of the sensor is adjacent to compressible material. Preferably, at least about 75% and more preferably at least about 85% of the perimeter is adjacent to the compressible material.

Figure 6:
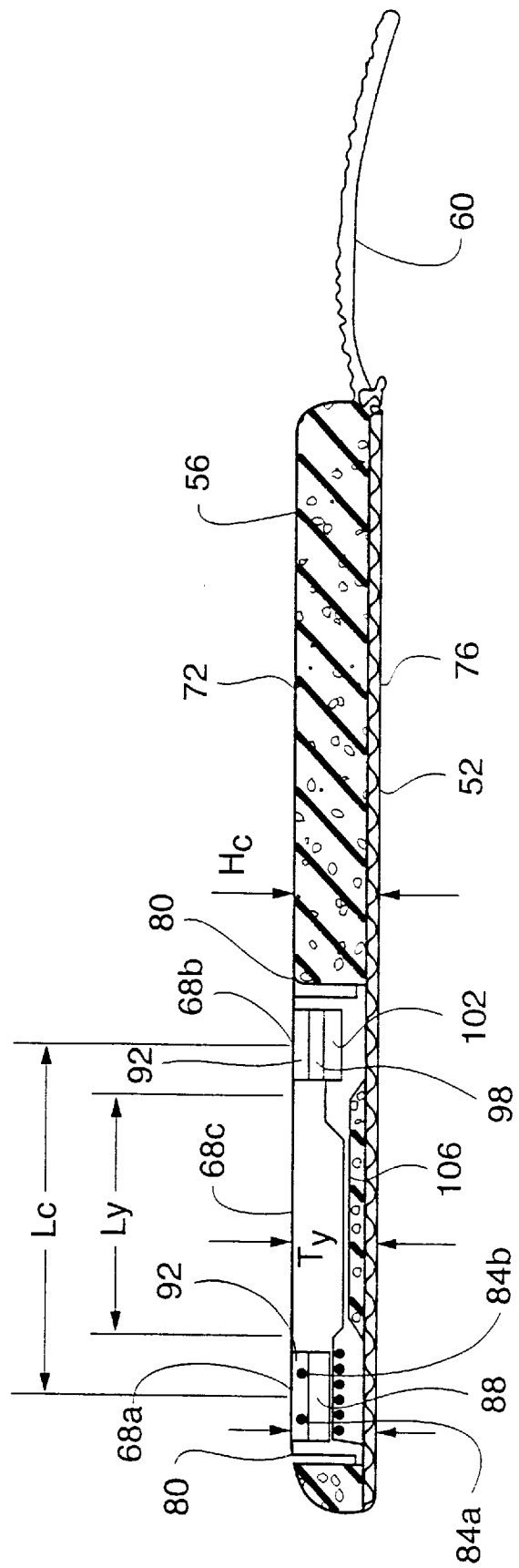
FIG. 6 is a cross-sectional view of the sensing device taken along line A—A in FIG. 1.

The emitter assembly 32 in the sensor 24 includes two emitters 84a,b having complementary spectral contents deposited on a substrate 88 and covered by a light transparent lens 92a to form a substantially level face of the sensor 24 for contacting the patient's skin. The emitter assembly 32 can be a single broad-band emitter broken into individual bands of red and infrared light by separate interference filters or, as shown in FIG. 6, separate emitters, such as LEDs. The emitters 84a,b emit radiation 96 in the direction shown in FIG. 8.

Returning to FIGS. 1–6, the detector 36 in the sensor preferably has a large dynamic range to receive the portion of the radiation 96 that is not absorbed by the bloodstream surrounding tissue. The preferred detector is a silicone photodiode 98 deposited on a substrate 102 and covered by a light transparent lens 92b. The silicone photodiode 98 has an output linearly proportional to the incident light level over a range of 10 decades of light intensity, has low noise levels, is lightweight and small, and responds to light through the visible region up to a wavelength of about 1,100 nm.

It is preferred that the front surfaces 68a,b,c of the lenses covering the emitters and detector and the yoke 40 physically contact the surface of the patient's skin. The housing encapsulating the emitters and detector includes the yoke 40 which carries conductive leads 106 for transmitting measurement information collected by the detector to the oximeter and a lip 42 extending around the perimeter of the base of the housing to secure the housing to the carrier 28 and to seal the upper and lower portions of the housing. The length "$L_Y$" of the yoke depends upon the body part to which the sensing device 20 is to be attached. The sensing device can be attached to a body part. To place the detector 36 and emitter assembly 32 in an opposing relationship as shown, the length of the yoke preferably ranges from about 1 to about 2 cm. This provides a distance "$L_C$" between the centers of the detector and the emitter assembly ranging from about 1.5 to about 4.0 cm and most preferably from about 2.5 to about 3.0 cm. The thickness "$T_Y$" of the yoke is less than the thicknesses of the opposing ends of the sensor as shown in FIG. 6, to facilitate flexure of the sensor when applied to the infant. Preferably the thickness "$T_Y$" ranges from about 0.05 to about 0.25 cm, more preferably from about 0.10 to about 0.20 cm, and most preferably from about 0.125 to about 0.175 cm. The housing is typically formed from an elastomeric material.

More detailed depictions of the various elements of the sensor are in FIGS. 13–20. The sensor includes the emitters 84a, b, the transparent lenses 92, upper and lower light impermeable members of the housing 300, 304, and lead frame 308 housing the detector and emitters and circuitry connecting the detector and emitters to the oximeter by way of the wire 312. The leadframe 308 is preferably composed of a conducting material, such as copper, and is preformed into a shape and size that can fit within the upper and lower light impermeable members of the housing. The leadframe 308 is etched to a preferred thickness ranging from about 5 to about 20 mil, with 7.5 mil being most preferred. The leadframe 308 is preferably formed from a single panel using a fixture and press that is custom designed to produce the desired leadframe configuration. The preforming of the leadframe to fit precisely within the upper and lower light impermeable members permits the sensor to have the substantially flat front surface 68, eases assembly of the sensor components into the upper and lower light impermeable housing members, and facilitates heat sealing of the upper and lower light impermeable housing members.

The upper light impermeable housing member 300 has a number of unique features. The member 300 has ribs 320 that are positioned between the conducting traces 324a–g of the leadframe 308 to provide electrical isolation of the traces 324 form adjacent traces and thereby prevent electrical shorting. The member 300 further includes bore 328 and contoured neck 332 and a contoured yoke 334, to direct the wire 312 and individual conductors on the traces and to minimize ambient light interference and light piping. The lenses 92 in the upper light impermeable housing member 300 are designed to precisely mate and be level with the front surface 68, of the member 300 to minimize any discontinuity on the sensor front surface.

The upper and lower light impermeable housing members 300, 304 are sized to precisely fit together with each having a lip 42 extending around its perimeter. The lip facilitates heat sealing of the upper and lower members. The lip 42 preferably extends a distance ranging from about 10 to 50 mil outward from the body of the upper member. The lip 42 can be in a tongue-and-groove configuration.

The compressible material 56 in the flexible carrier means 28 physically contacts the patient's skin thereby cushioning the contact between the sensor assembly 20 and the skin. The compressible material has a compression setting that, upon application of a predetermined pressure to the material, substantially conforms to the surface contacting the compressible material. The material preferably is characterized by an indentation force of no more than about 100 lbs/50 in$^2$, more preferably no more than about 90 lbs/50 in$^2$, and most preferably ranging from about 12 to about 75 lbs/50 in$^2$. According to industry standard ASTM D-3574-86, the indentation force is the force required to produce a 25% deflection of the compressible material. The compressible material 56 preferably has a plurality of void spaces to permit compression. More preferably, the volume occupied by the compressible material 56 is at least about 50% by volume void space and most preferably the amount of void space ranges from about 60 to about 80% by volume. Preferred compressible material is open or closed cell foam, neoprene, rubber, fabric, and composites thereof, with foam being most preferred. To provide the necessary degree of compressibility, the compressible material preferably has a thickness "$T_C$" of at least about 0.4 cm and more preferably ranging from about 0.4 to about 1.5 cm. These features provide a compressible material having a density ranging from about 1.0 lbs/ft$^3$ to about 3 lbs/ft$^3$ with about 1.5 lbs/ft$^3$ being most preferred; an ultimate tensile strength ranging from about 15 to about 50 psi, with about 30 psi being most preferred; an ultimate elongation at break ranging from about 250 to about 500% with about 300 to about 450% being most preferred; and a tear resistance ranging from about 2 to about 10 ppi with about 3 to about 5 ppi being most preferred.

The backing material 52 in the flexible carrier 28 is adhesively bonded to the compressible material and sensor and imparts tensile strength to the carrier. A suitable backing material is highly flexible and has a relatively high tensile strength. The preferred backing material is cloth, foam, and composites thereof. The most preferred carrier 28 is formed from a composite material manufactured by a company having the tradename "POSEY COMPANY". This composite material has a soft cloth backing material attached to a soft, highly compressible foam.

The attachment strap 60 in the flexible carrier 28 includes a plurality of hooks that engage a plurality of loops on the free surface 76 of the backing material 52. The attachment strap is preferably a material sold under the trademark "VELCRO". As will be appreciated, the relative locations of the hooks and loops is not critical provided that the hooks and loops do not contact the skin and a suitable range of size adjustability is provided. Thus, the plurality of hooks can be located on the backing material 52 and the loops on the attachment strap 60. As will also be appreciated, the attachment strap 60 can fasten to the backing material in a number of other ways, such as by an adhesive coating on the strap or free surface 76 of the backing material.

The sensing device 20 can be relatively small and lightweight for use with infants. The length "$L_B$" of the backing material 52 preferably ranges from about 7.5 to about 12.5 cm. The length "$L_A$" of the attachment strap 60 preferably ranges from about 2.5 to about 6.0 cm. The width "W" of the carrier 28 preferably ranges from about 1.25 to about 3.00 cm. The weight of the sensing device 20 is preferably about 1.5 g or less and most preferably ranges from about 0.5 to about 1.0 g.

Figure 7:
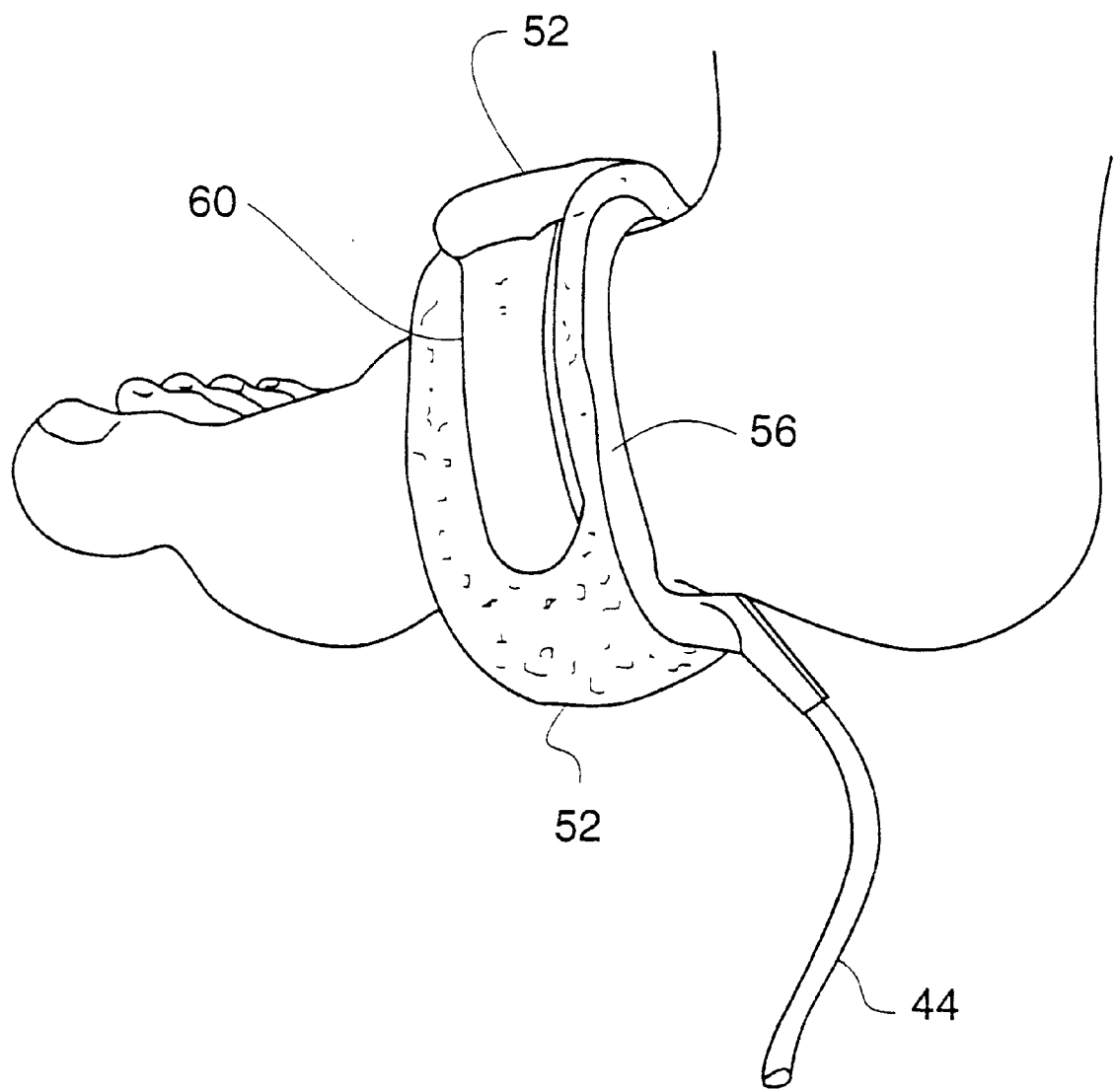
FIG. 7 is a perspective view of the sensing device contacting the foot of a premature infant.
Figure 8:
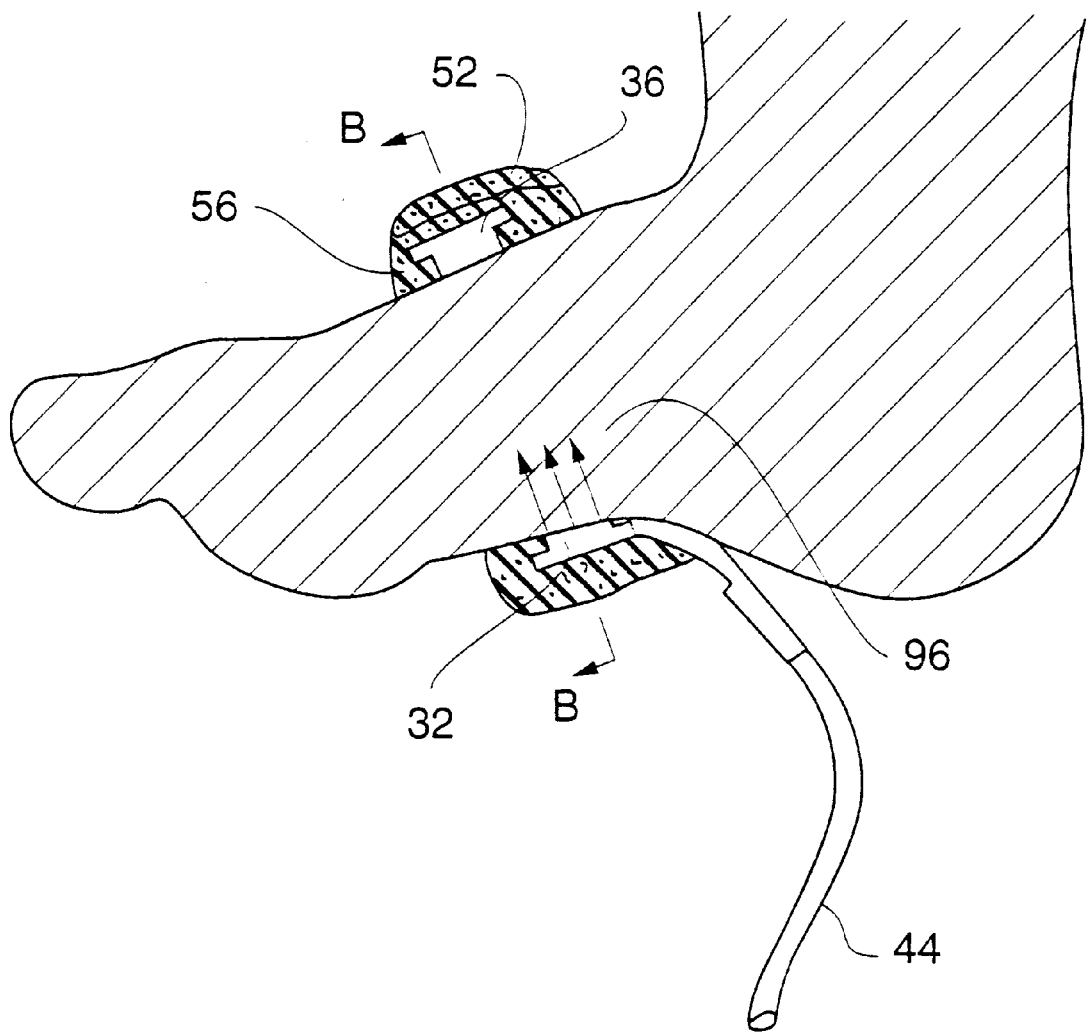
FIG. 8 is a cross-sectional view taken along the length of the foot in FIG. 7.
Figure 9:
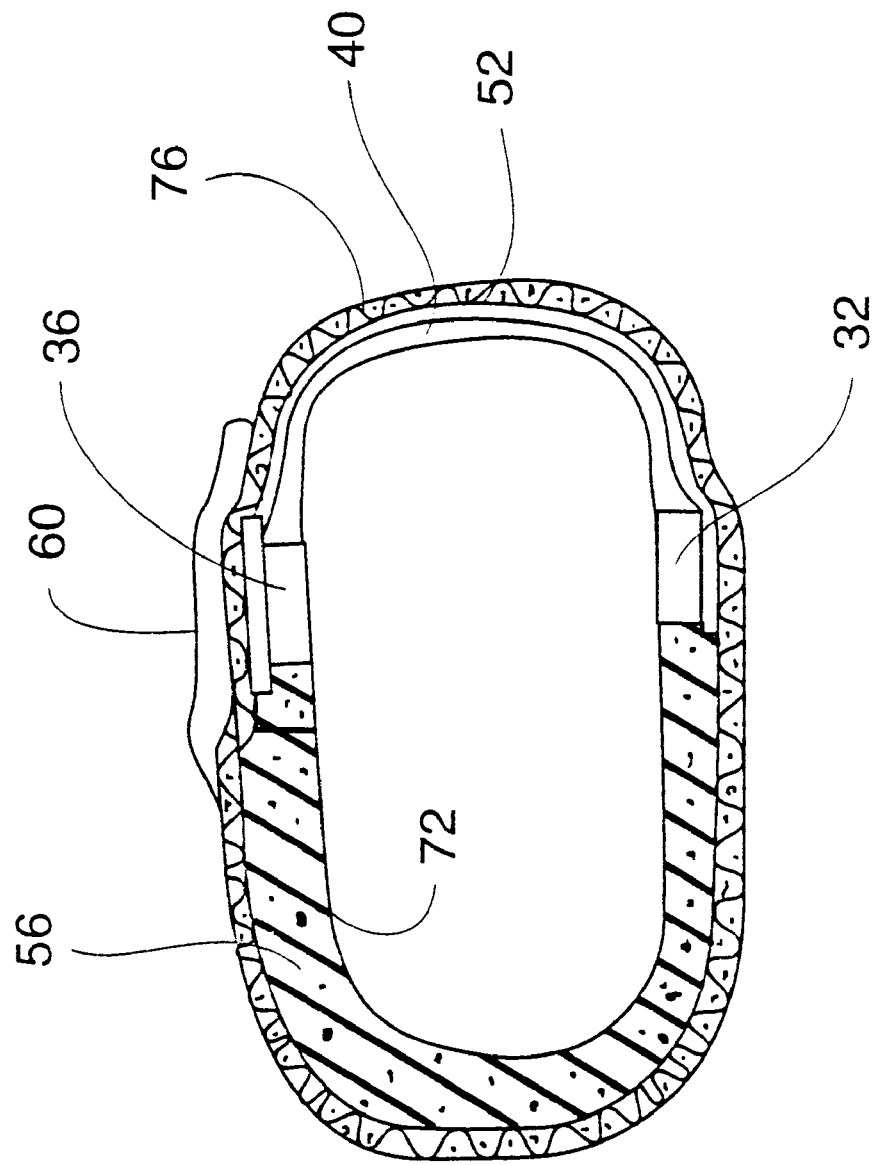
FIG. 9 is a cross-sectional view taken along line B—B in FIG. 8.

Referring to FIGS. 7–9, the method for using the sensing device 20 will be discussed. Although the sensing device 20 is discussed with reference to an infant, the sensing device can also be used in a variety of other applications where skin sensitivity is a concern, such as to measure the blood oxygen content of burn victims.

The flexible carrier 28 is attached to a body part of the patient such that the detector 36 and emitter assembly 32 are in a substantially opposing relationship. To attach the carrier means 28, the attachment strap 60 is attached to the free surface 72 of the backing material 52 as shown in FIG. 7. When attaching the carrier 28 to the body part, it is important not to pull the carrier means 28 too tightly around the body part to avoid impairment of blood flow. Preferably, the pressure exerted on the body part by the sensing and compressible material is no more than about 3 psi and most preferably no more than about 1 psi. Under these pressures, the thickness of the compressible material will decrease (i.e., compress) by an amount ranging from about 20 to 40% of the original (uncompressed) thickness. As shown in the FIGS. 8–9, when the carrier 28 is attached to the body part, the upper surface 72 of the compressible material is substantially level with the front surfaces 68a,b of the detector and emitters. Thus, the front surfaces 68a,b of the lenses covering the detector and emitters are generally substantially level relative to one another.

Radiation 96 is passed from the emitters through the infant's bloodstream and surrounding tissue with a portion of radiation being absorbed by the bloodstream and surrounding tissue (i.e., absorbed radiation portion) and another portion being passed by the bloodstream and surrounding tissue (i.e., unabsorbed radiation portion).

The unabsorbed radiation portion is received by the detector 36. A signal is generated by the detector in response to the contact of the unabsorbed radiation portion with the detector.

The signal is transmitted through the conductive leads 44 to an oximeter processing and display unit (not shown) that processes the signal and determines the oxygen content of the bloodstream.

Figure 10:
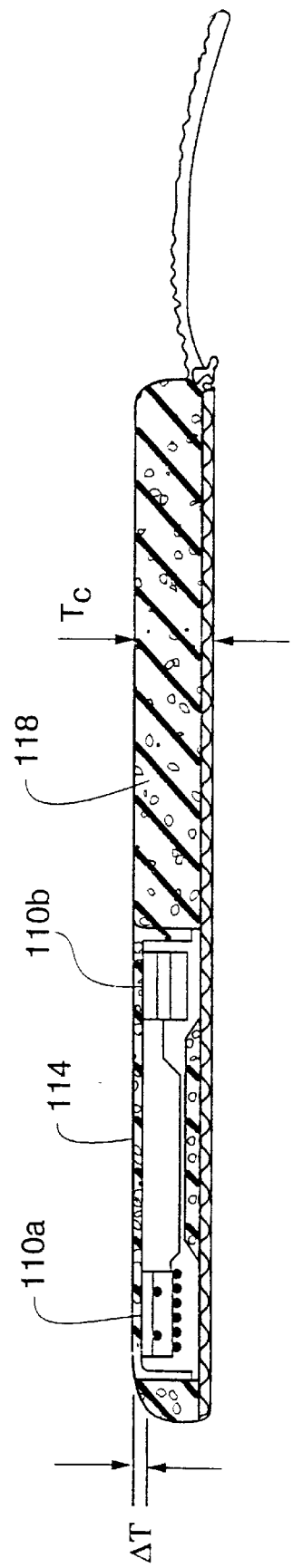
FIG. 10 is a cross-sectional view taken along line A—A of another embodiment of the sensing device of the present invention.

An alternative embodiment of the sensing device present invention is depicted in FIG. 10. The alternative embodiment is substantially the same as the embodiment discussed above except that the front surfaces of the lenses covering the detector and emitter means 110a,b are offset by a distance "ΔT" from the front surface 114 of the compressible material 118. The distance "ΔT" is selected such that, when the compressible material is compressed by attachment to the body part of a patient, the thickness "Tc" of the compressed material above the backing material is no less than the maximum thickness of the sensor above the backing material. It is preferred that the front surfaces 110a,b be substantially coplanar with the front surface 114 of the compressed compressible material. The distance "ΔT" is preferably no less than about 40% and more preferably no less than about 30% of the thickness "$T_C$" of the compressible material. In most applications, the distance ΔT ranges from about 0.3 to about 0.6 cm and most preferably from about 0.4 to about 0.5 cm. In this embodiment, the thickness of the sensor is no more than the height of the cavity walls when the compressible material is compressed to the desired degree.

Figure 11:
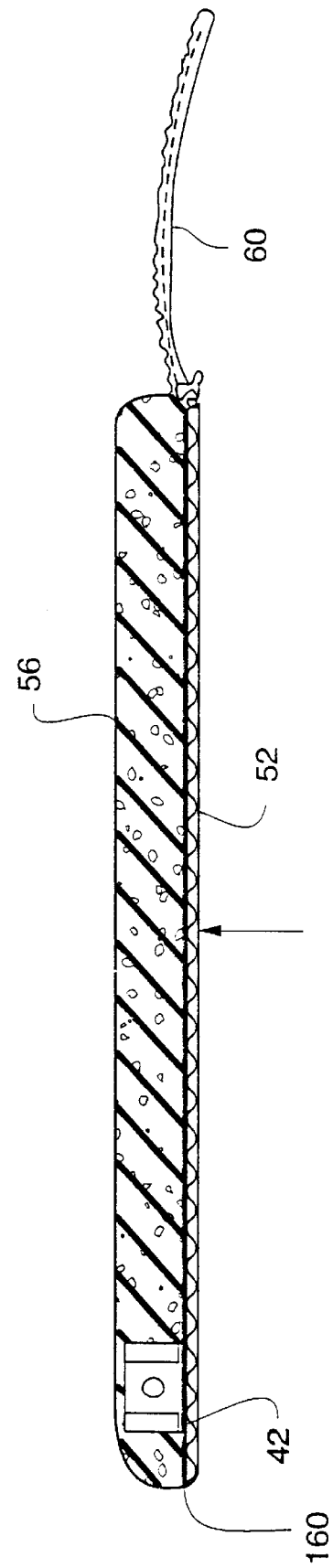
FIGS. 11 and 12 are side and top views of yet another embodiment of the sensing device.
Figure 12:
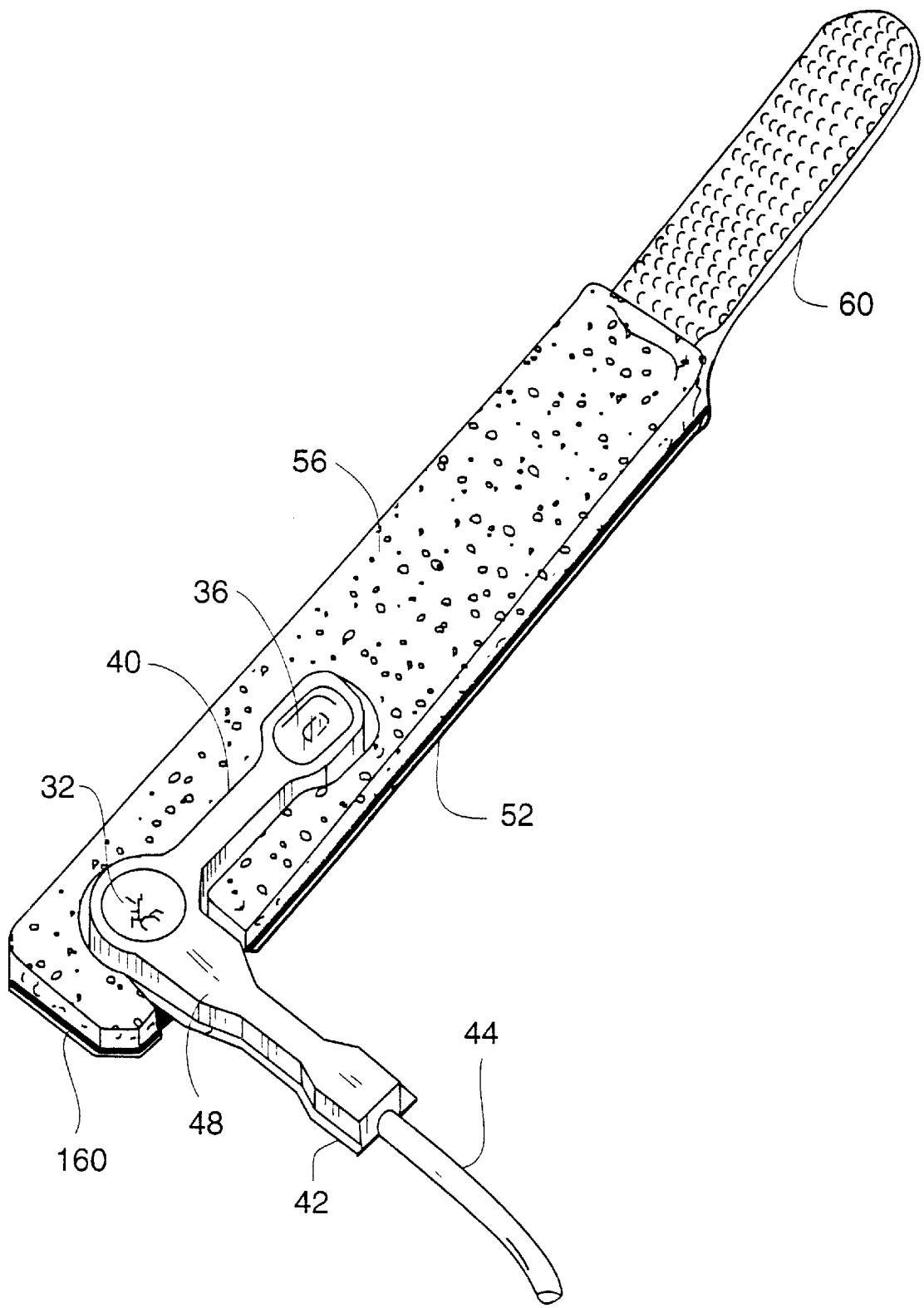
Figure 13:
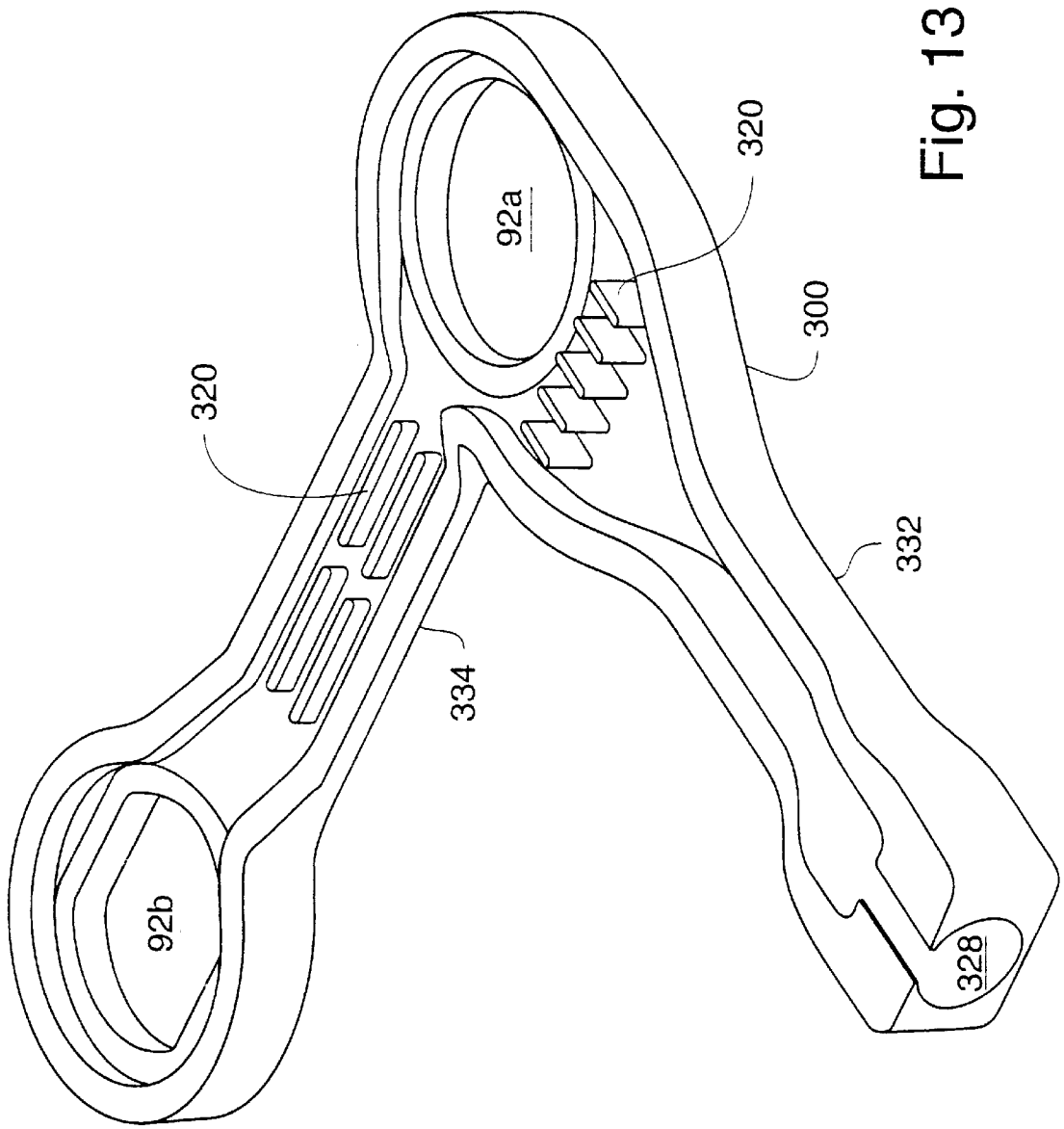
FIGS. 13–20 depict the various components of the sensing means.
Figure 14:
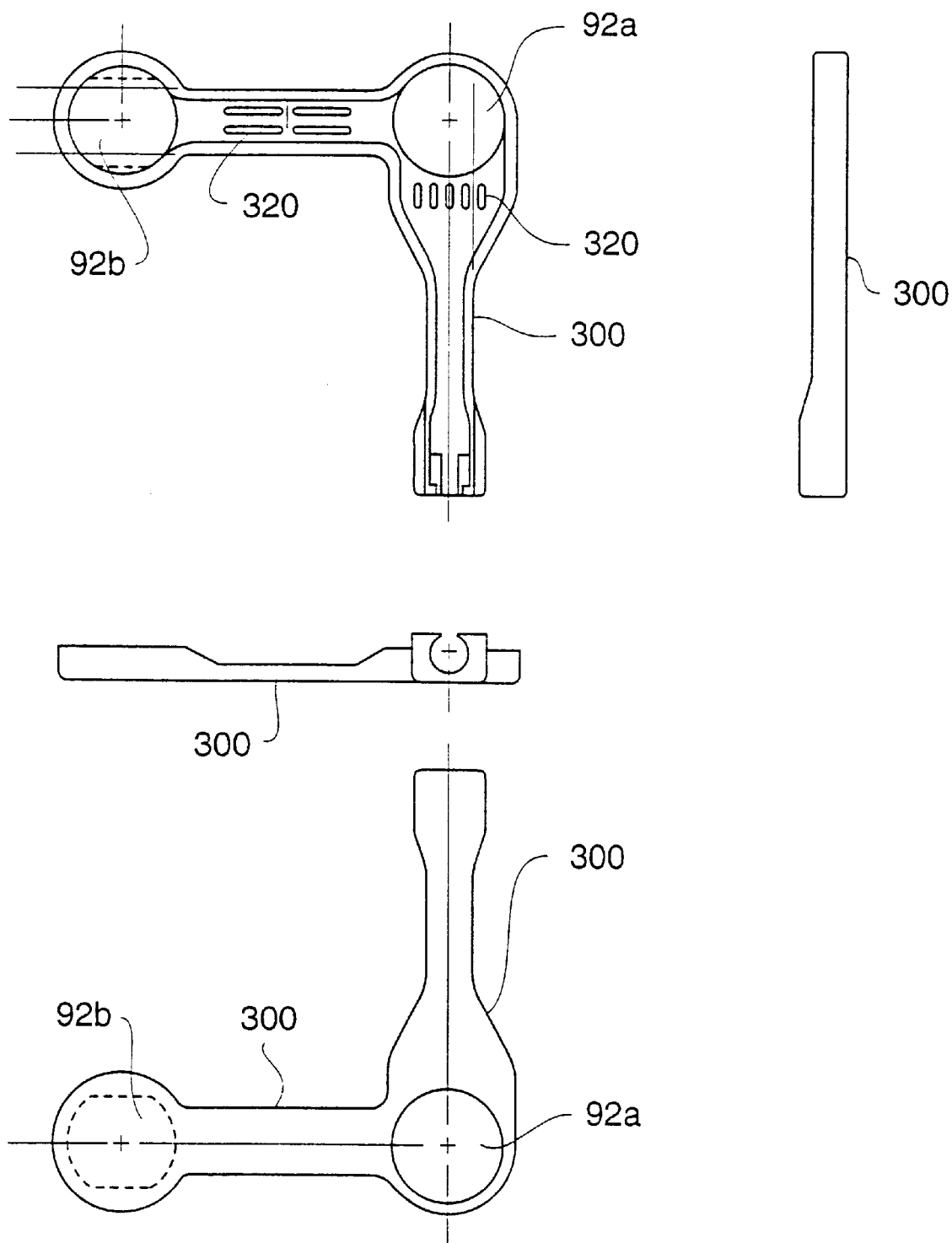
Figure 15:
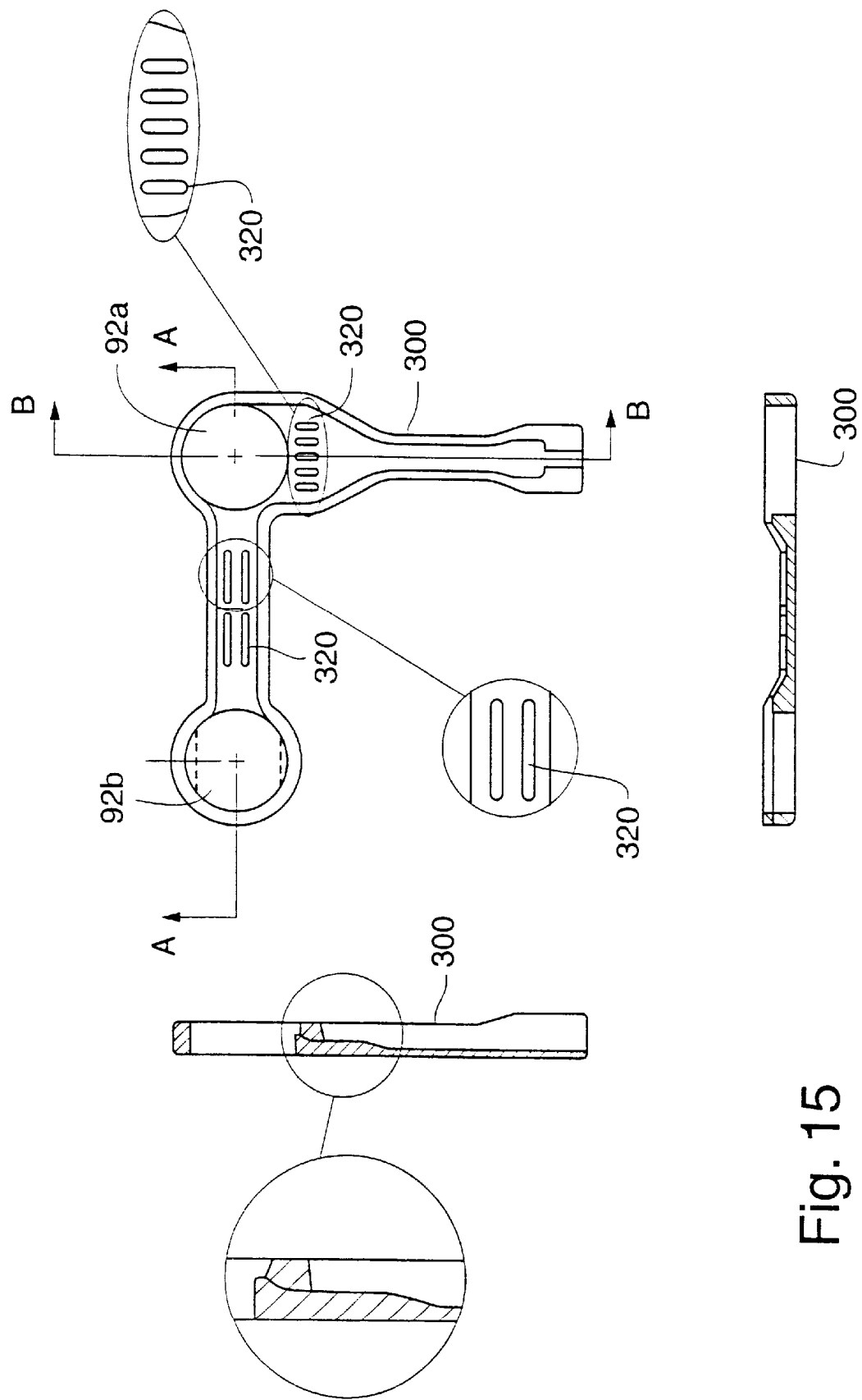
Figure 16:
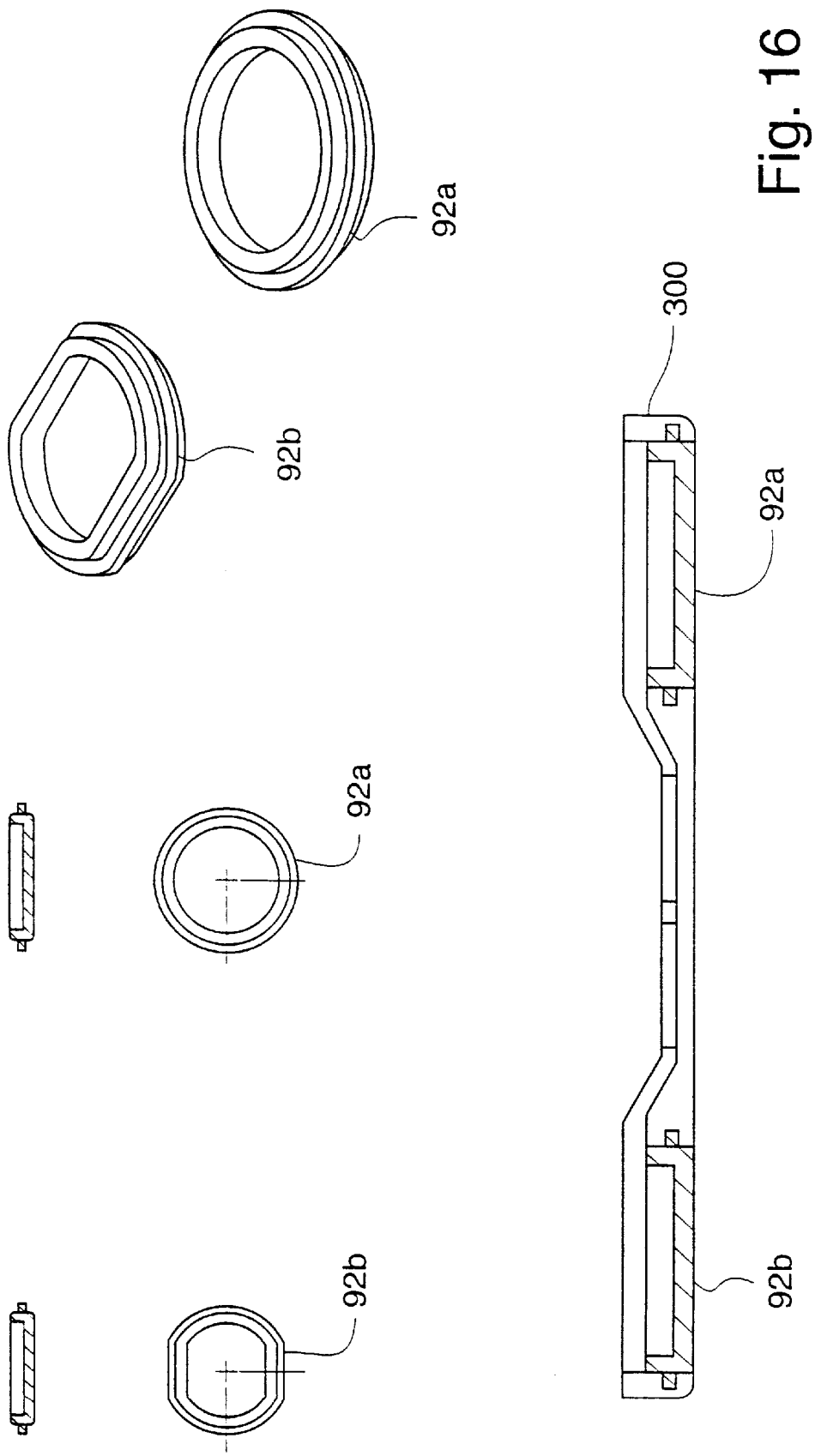
Figure 17:
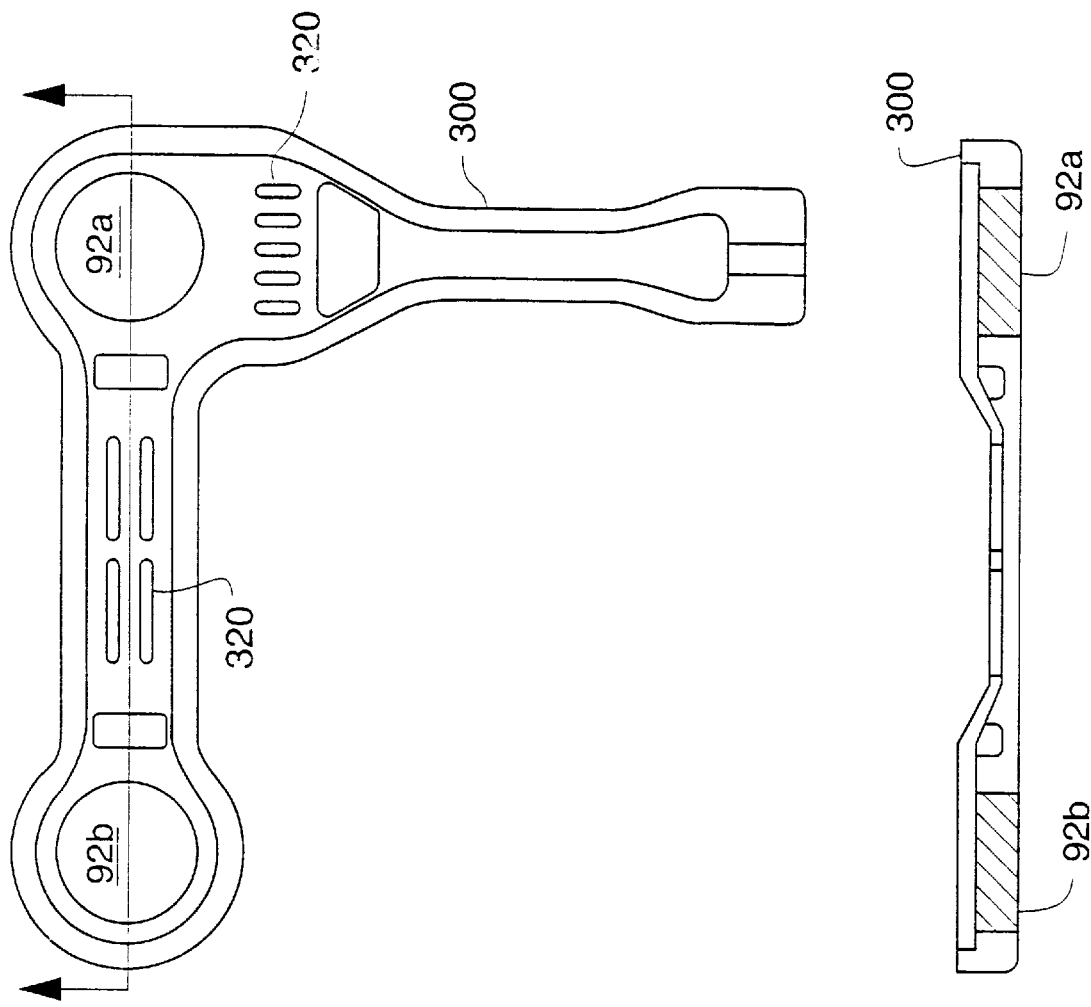
Figure 18:
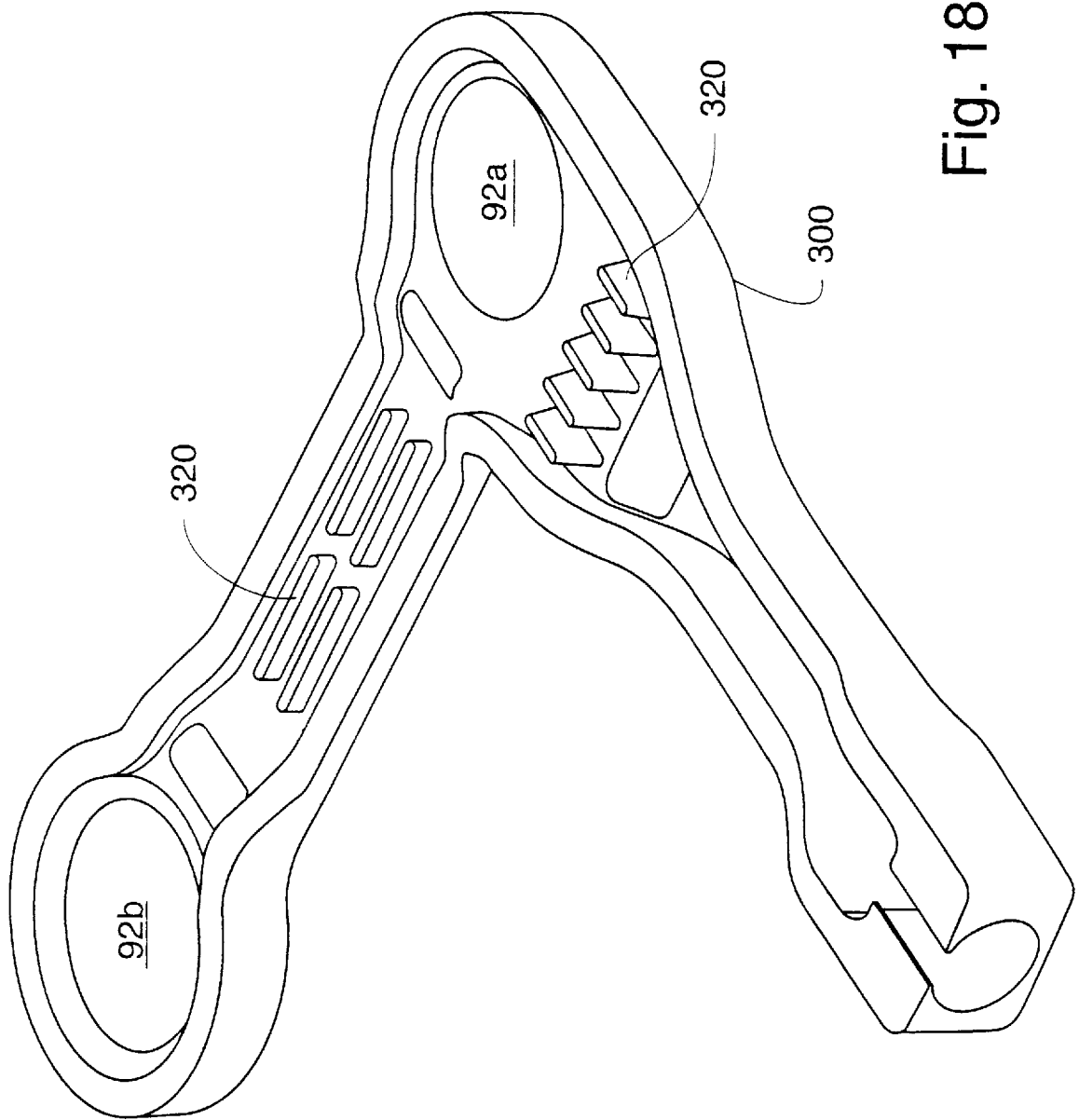

Another embodiment of the present invention is depicted in FIGS. 11 and 12. The embodiment is substantially the same as the embodiment shown in FIGS. 1–9, except that an additional light impermeable layer 160 is included to reduce the effects of ambient light. The light impermeable layer 160 is located between the compressible material and backing material and extends the length "$L_B$ and width "W" of the sensing device. The layer 160 can be formed from a variety of materials, including fabric, foam and composites thereof. Additionally, a light opaque adhesive can be located in the recess or on the rear side of the lower light impermeable housing member 304 to retain the housing in the recess. The layer 160 is substantially opaque to ambient light, preferably blocking from about 75 to about 100% and more preferably from about 90 to about 100% of the ambient light from passing through the layer 160.

In yet another alternative embodiment, the compressible material 56 can be substantially opaque to light. In this embodiment, it would be unnecessary to have a separate light impermeable layer 160 as shown in FIG. 11.

In a further alternative embodiment shown in FIGS. 21–24, the lower and upper light impermeable members have different configurations from the lower and upper light impermeable members in FIGS. 13–20 and incorporate a thin layer of opaque material 408 in the lower light impermeable housing member 400 to further reduce noise caused by ambient radiation. The lower light impermeable housing member 400 includes wells 412 to receive the portions of the leadframe housing the detector and emitters. The lower light impermeable member 400 is also contoured to substantially eliminate component alignment problems. A ridge 410 surrounding the lower light impermeable housing member 400 provides alignment with a matching groove surrounding the perimeter of the upper light impermeable housing member 404 to facilitate assembly of the lower and upper light impermeable housing members.

In a further alternative embodiment shown in FIGS. 29–31, the upper light impermeable housing member 500 includes a wider lip 504 than in previous embodiments and a rib 516 having variable widths. The lip 504, as shown in FIGS. 31–32, has a variable width around the perimeter of the upper light impermeable housing member 500. Thus, the width "$W_1$" shown in FIG. 32 is less than the width "$W_2$" shown in FIG. 31. The lip 504 projects both inwardly and outwardly of the upper portion 512 of the upper light impermeable housing member 500. The ribs 516*a,b* have a width varying between the width "$W_3$" and "$W_4$". The nubs 508*a–c* have the greater width "$W_4$" while the portions 524*a,b* of the rib located between adjacent nubs have the lesser width "$W_3$". The nubs 508*a–c* retain the lead frame in position by applying pressure to the opposing sides of the traces in the lead frame. This is accomplished by positioning nubs of one rib adjacent to nubs of an adjacent rib. The distance "D" between adjacent nubs is less than the width of the trace to be received between the nubs. The lip 504 also has nubs 520*a–c* positioned adjacent to the nubs 508*a–c* of the adjacent rib 516*a* and nubs 520*d–f* positioned adjacent to the nubs 508*d–f* of the adjacent rib 516*b*. The fact that the upper light impermeable housing member is composed of a relatively elastic thermoplastic resin permits the traces to apply pressure to and deform the nubs 508*a–f* and 520*a–f* when the traces are received between the nubs.

In a further alternative embodiment shown in FIGS. 25–28, the various leadframes 360*a–d* stamped from a conductive sheet 36 are selectively etched to provide at least two distinct thicknesses in each leadframe. In certain portions of each leadframe, it is desired to have a smaller thickness to impart flexibility to the leadframe and in other portions it is desired to have a larger thickness to provide heat transfer away from electrical components. FIG. 27B depicts the parts 364*a–d* of each leadframe 360*a–d* for which a greater thickness is desired, and FIG. 27C the parts 368*a–d* of the leadframe 360 for which a smaller thickness is desired. FIG. 27B depicts the thicker part of the leadframes on the conductive sheet with the thinner parts removed, and FIG. 27C depicts the thinner parts of the leadframes with the thicker parts removed. FIG. 27C depicts the outline of the conductive sheet 361 in dashed lines. The preferred thickness of the parts 364*a–d* ranges from about 10 to about 20 mils, with 15 mils being most preferred. The preferred thickness of the parts 368*a–d* ranges from about 5 to about 10 mils, with 7.5 mils being most preferred.

Figure 27A:
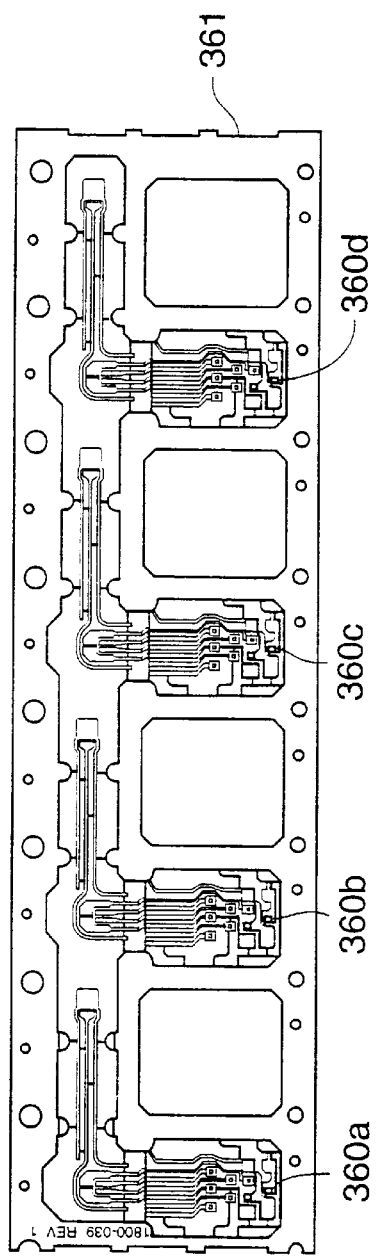
Figure 27B:
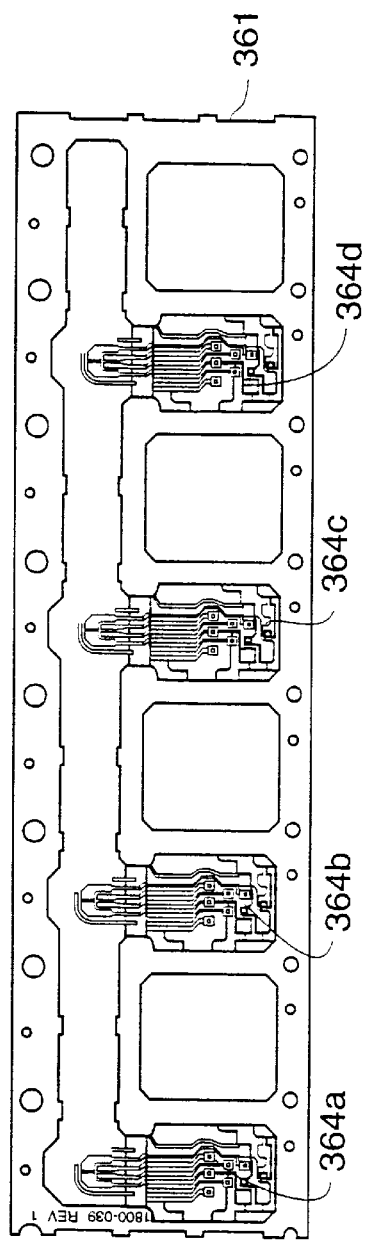
Figure 27C:
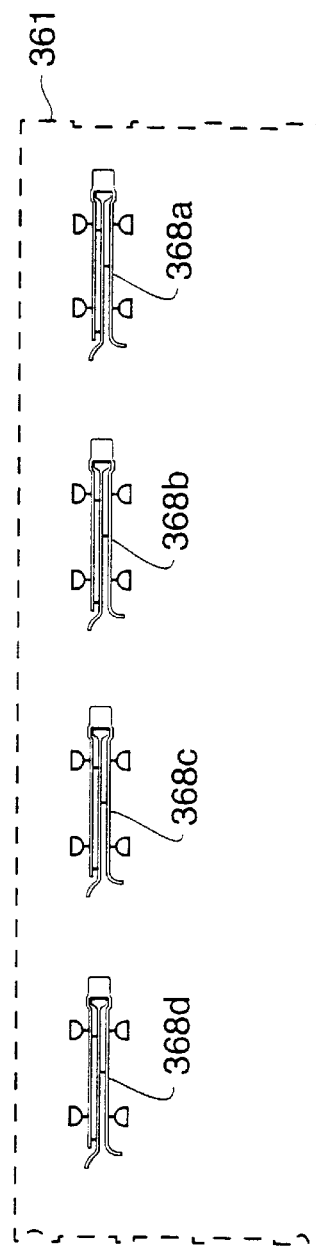

The variable thickness in the leadframe 360 can be formed without forming two or more of the parts of the leadframe and soldering or welding them together by selectively etching only those parts in FIG. 27C, typically while the leadframes 360*a–d* are still attached to the conductive sheet 361. The leadframe 360 is therefore substantially free of joints, such as solder and weld joints. Thus, the leadframes before etching have a substantially uniform thickness equivalent to the thickness of the conductive sheet. The partial etching can be performed by applying an etchant to only the parts of the leadframe in FIG. 27C, by applying a masking material, such as dry film laminars to the leadframe parts in FIG. 27B before the etchant is applied to the leadframe or by etching the parts 368*a–d* of the leadframe for a longer period of time than the parts 364*a–d*.

Alternatively, the variable lead frame thickness can be formed by skiving (i.e., modifying the cross section of the sheet by suitable techniques before stamping out of the lead frames) and coining (i.e., deforming the sheet or lead frame to produce different cross sections).

Figure 28:
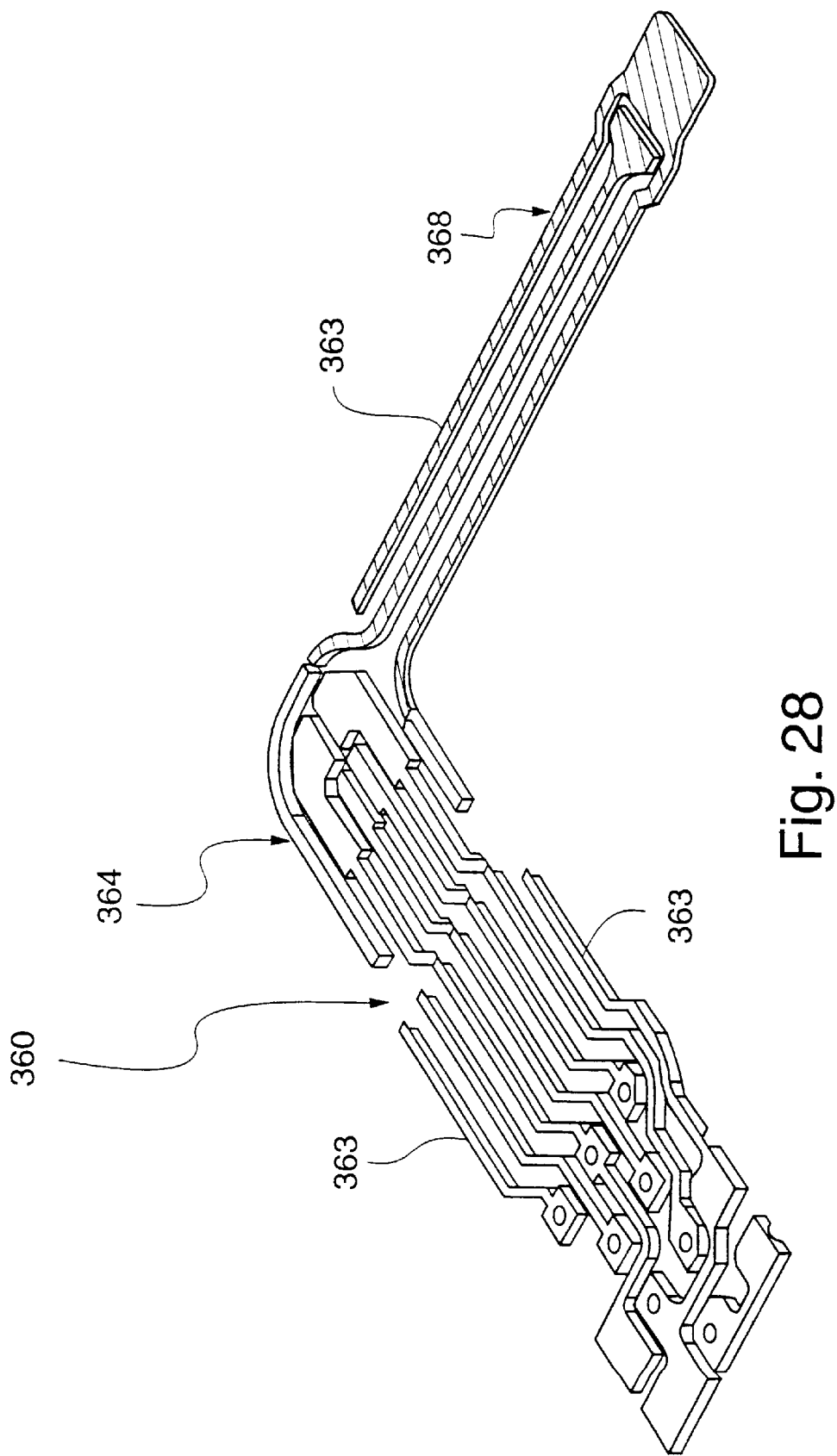

FIG. 28 depicts a leadframe 360 after removal from the conductive sheet. The leadframe has been trimmed of support members used during formation of the leadframe to support the various traces 363 and is, therefore, configured for assembly into the sensing device. The thinner portions of the leadframe 368 are highlighted by thatched lines. The thicker portions 364 are not highlighted by thatched lines.

Figure 19:
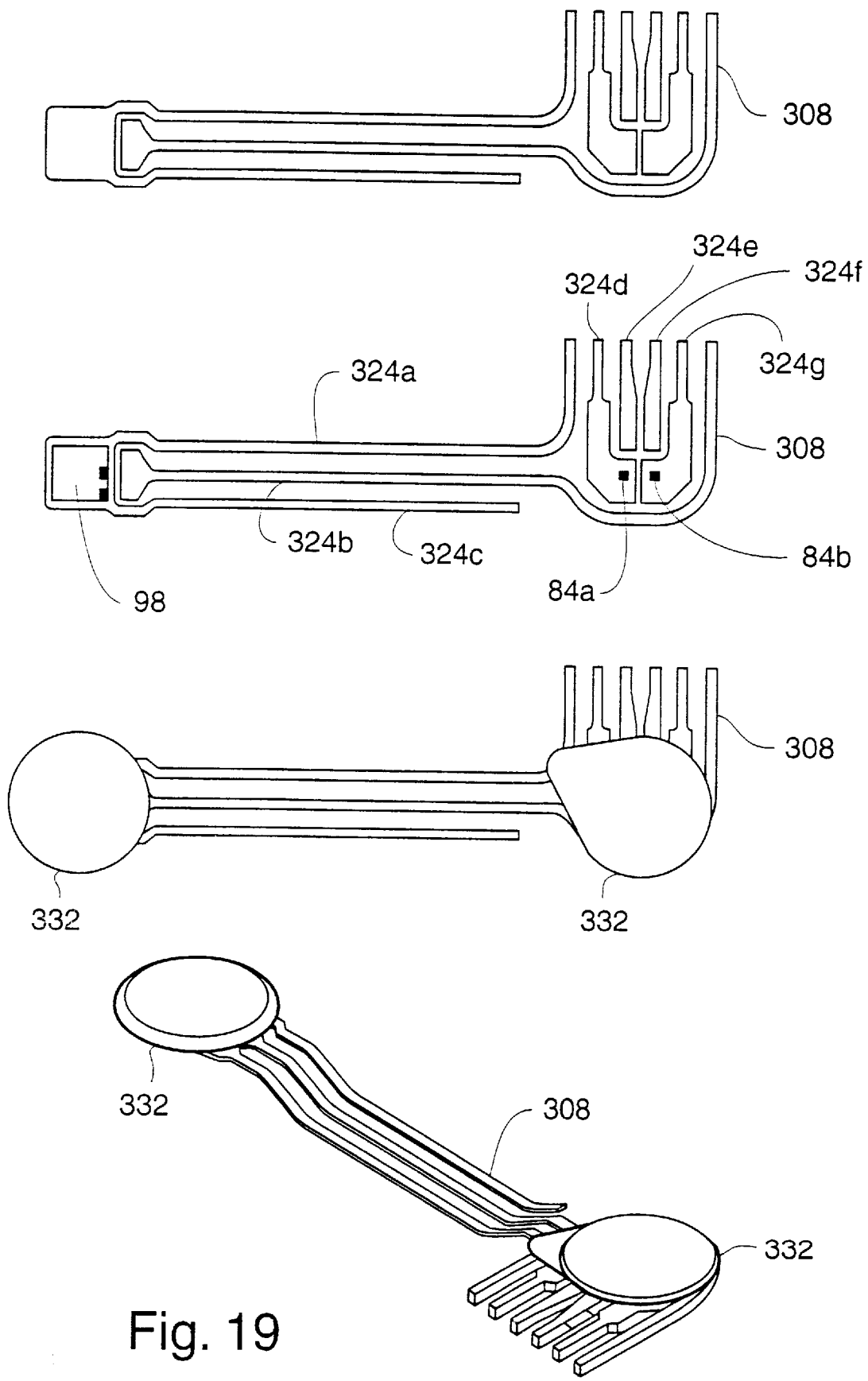
Figure 20:
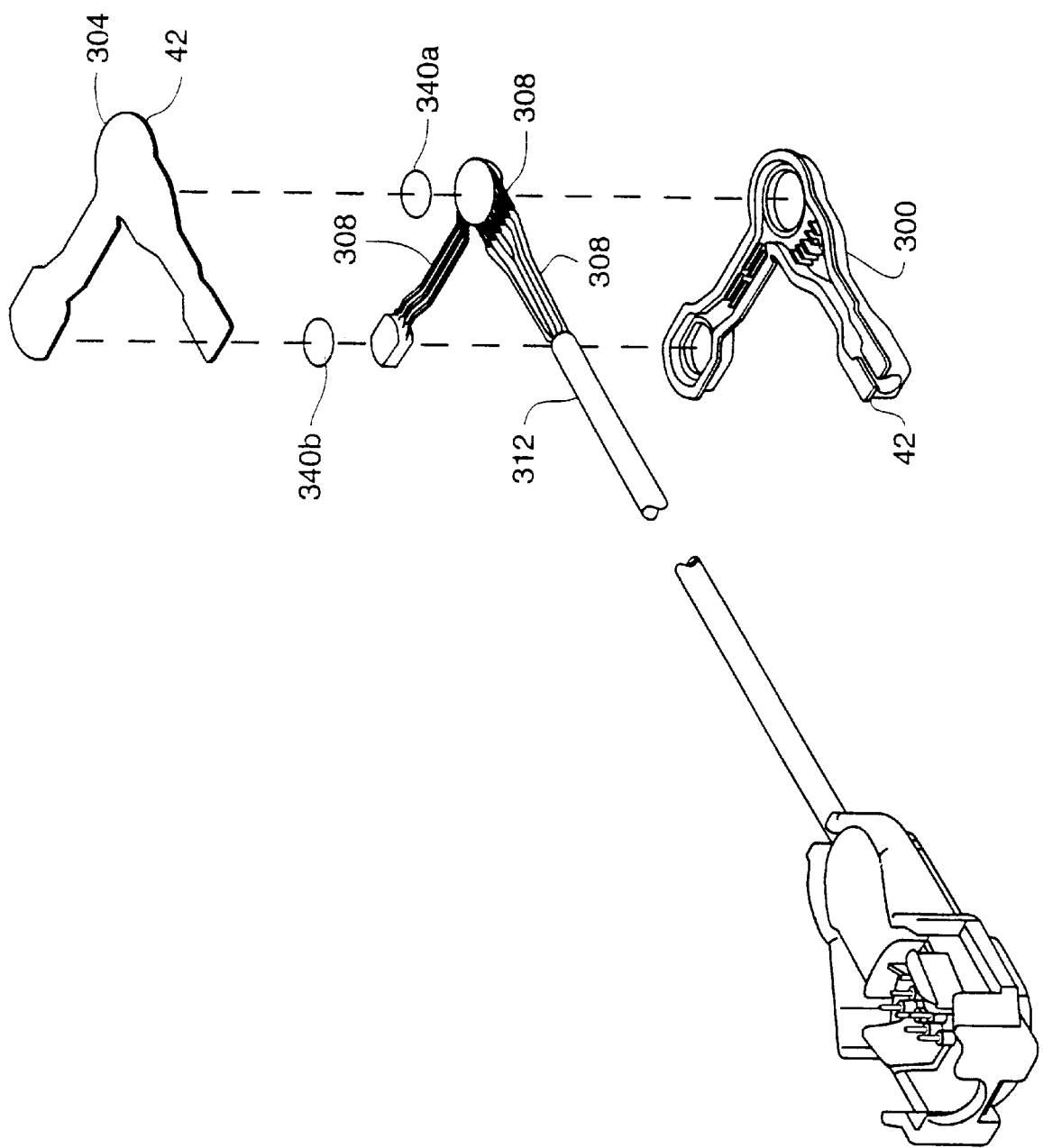
Figure 21:
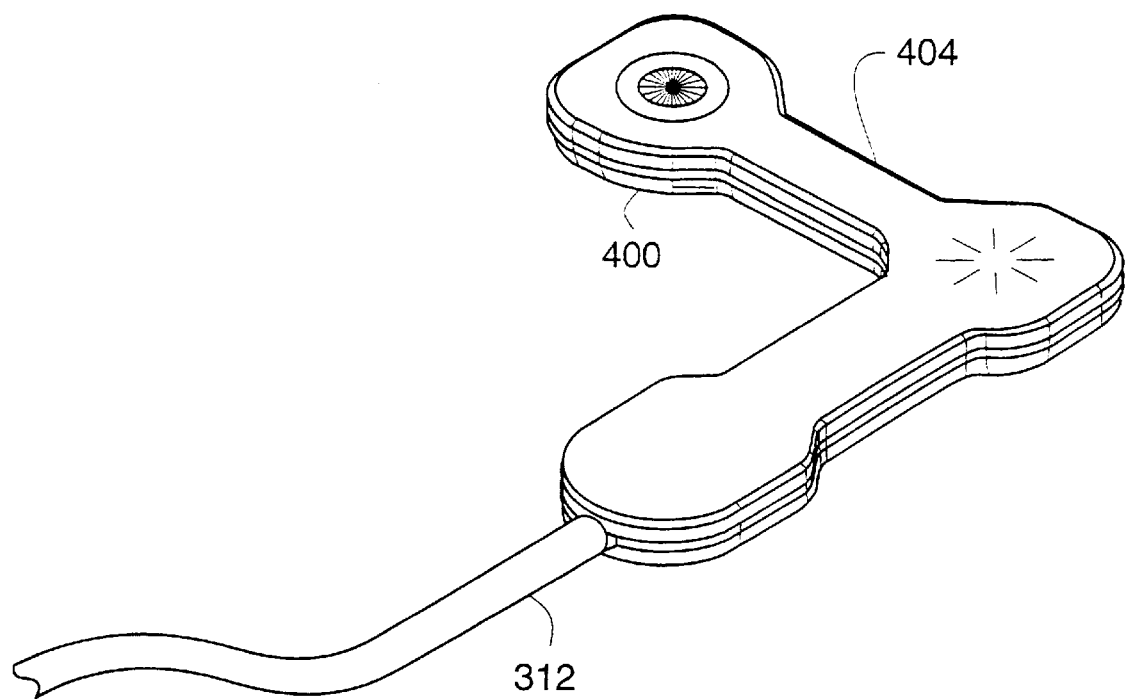
Figure 23:
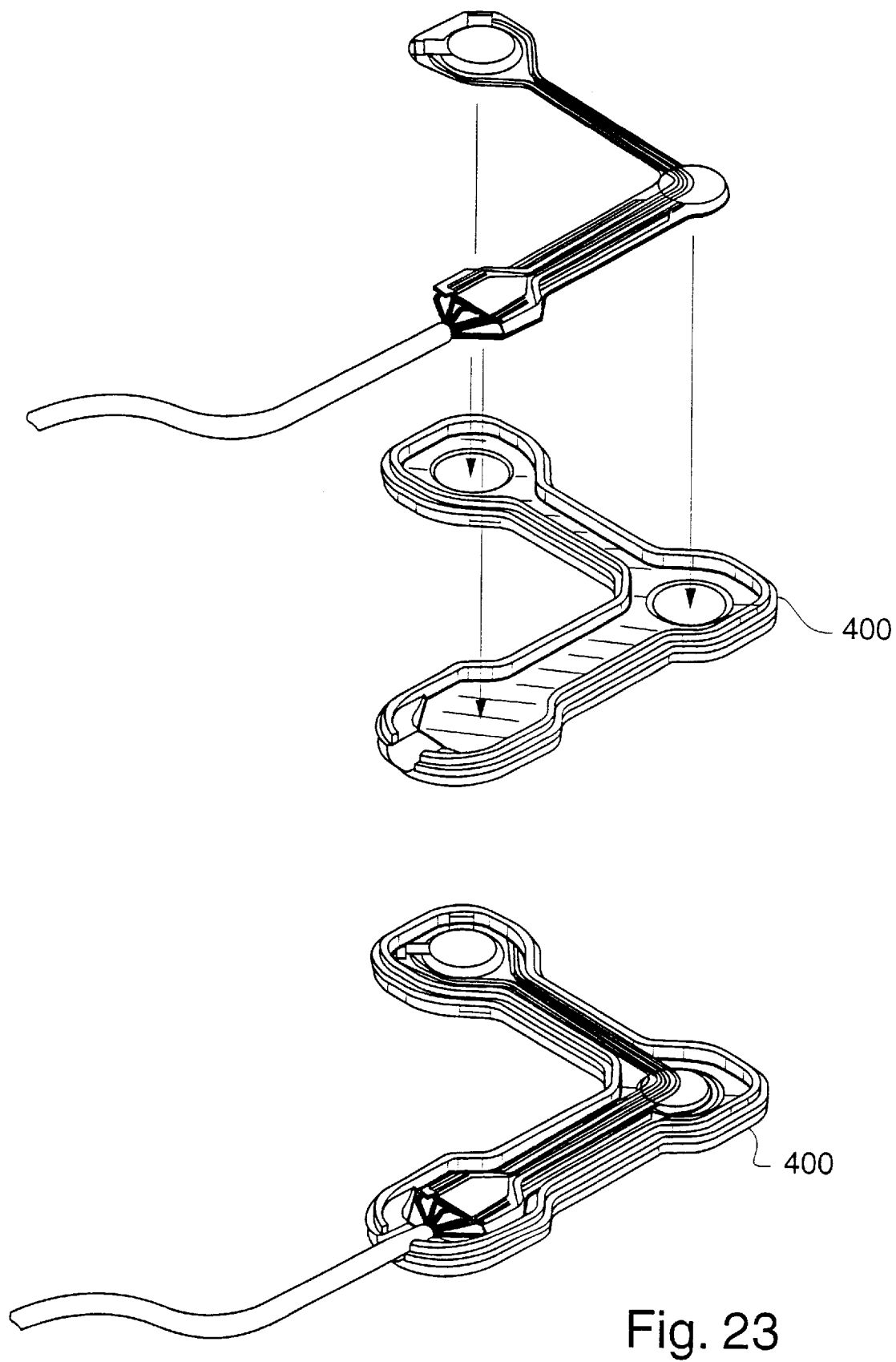
Figure 24:
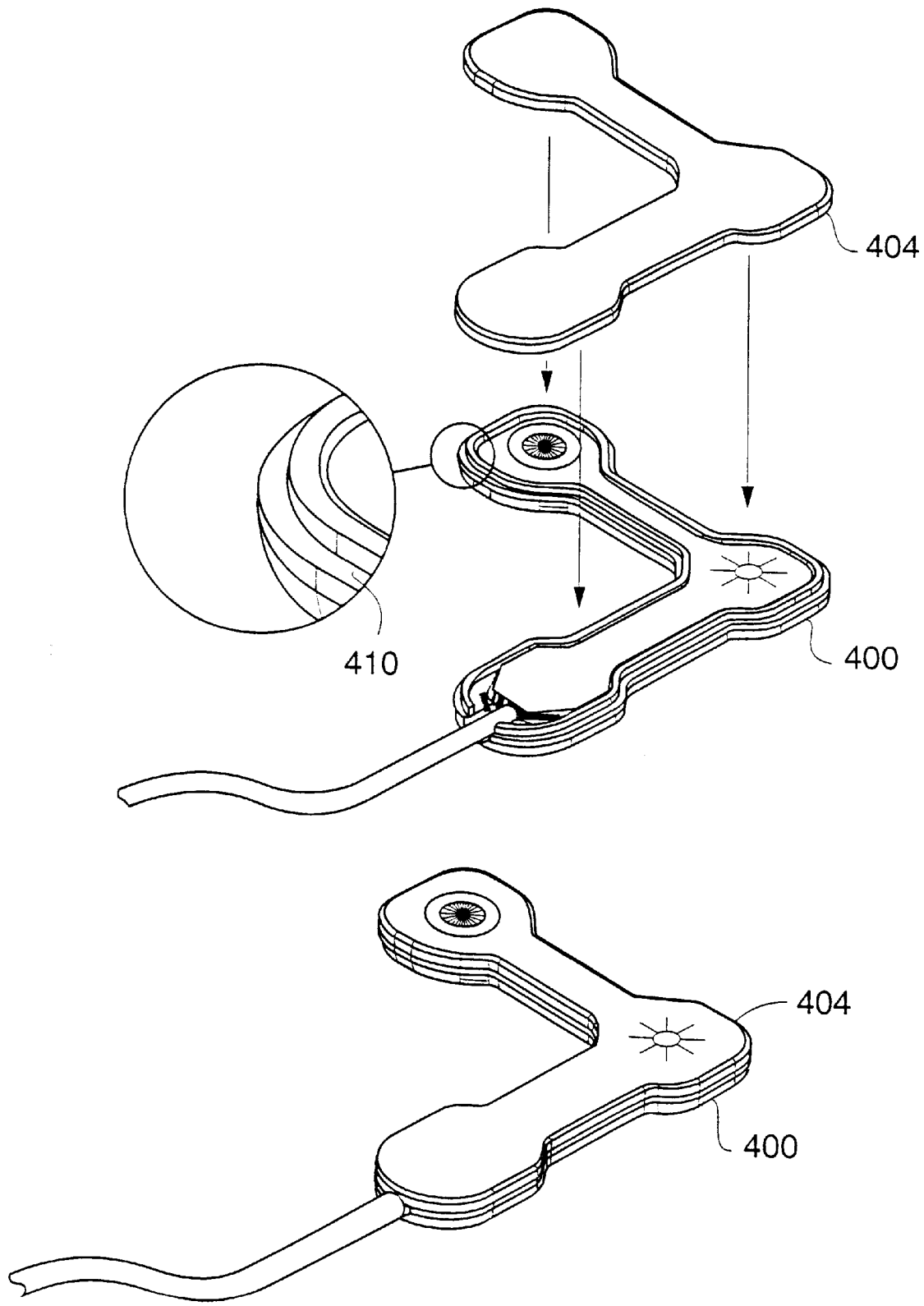
Figure 25:
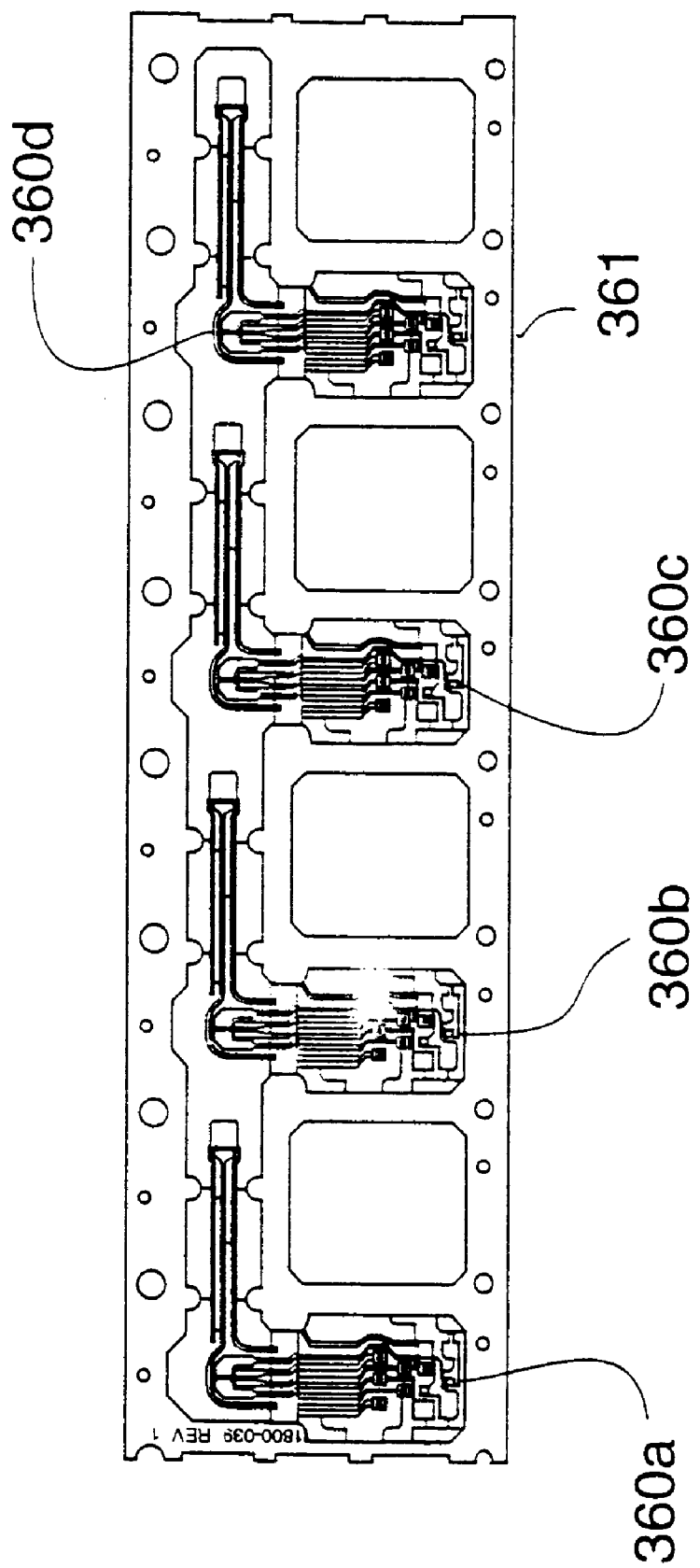
FIGS. 25–28 depict an embodiment of the leadframe of the present invention.
Figure 26:
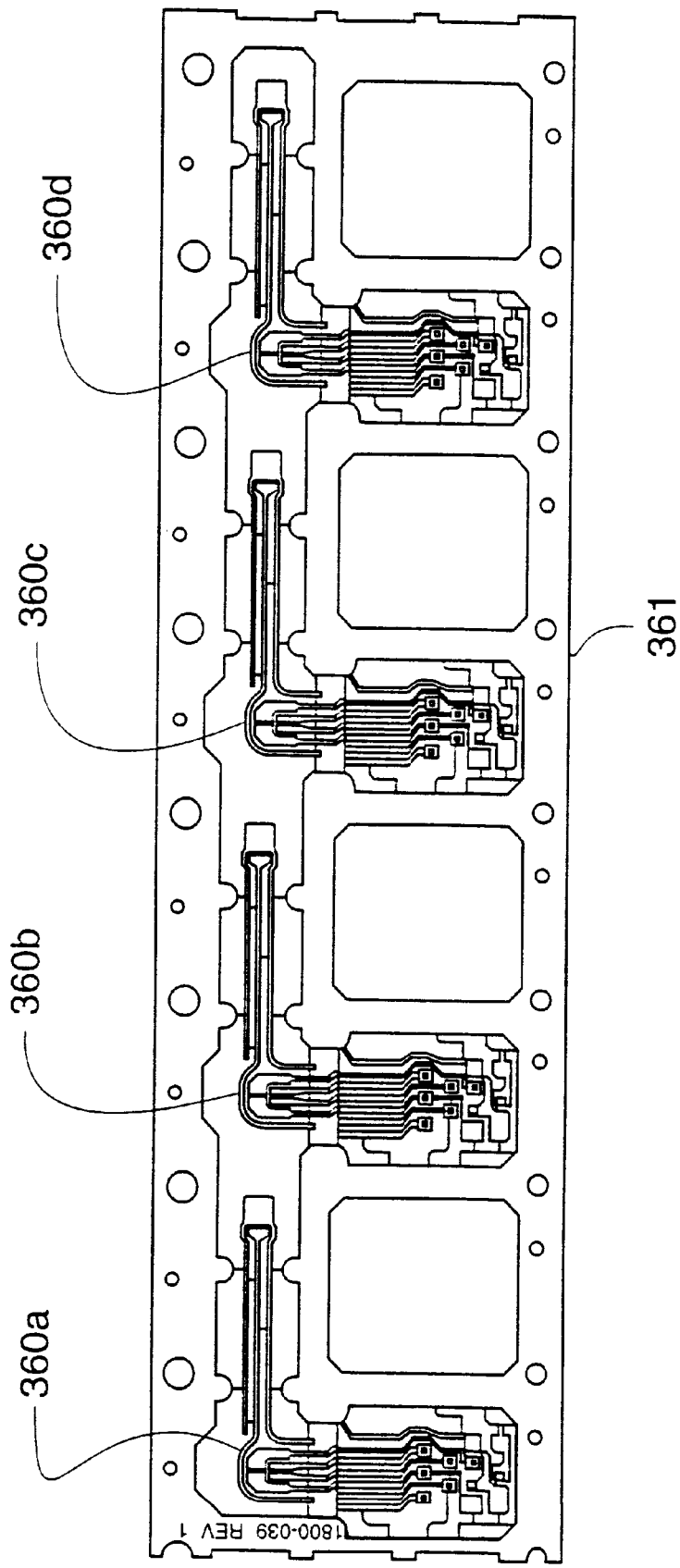

The invention further includes a method for assembling the sensing device 20 shown in FIGS. 19–20. In a first step, the cavity is formed in the compressible material using a cutting die have the same size and shape as the sensor. The compressible material is removed down to the backing material. The layer of the backing material is not cut to provide a way to attach the carrier to the rear of the sensor.

The various parts of the sensor are assembled before the lower light impermeable housing member is attached to the backing material in the cavity. The lenses 92 are formed by injection molding. The lenses 92 are then placed on core pins in another injection molding tool and the body of the sensor is formed around the lenses 92 in an insert molding operation. Although the substantially light opaque resin forming the body of the sensor is injected into the injection molding tool at a temperature at or above the melting point of the resin, the resin causes only partial melting of the lenses 92 at the perimeter of the lenses 92. The partial melting of the lenses 92 causes the formation of a tight seal between the lenses 92 and the adjacent portions of the substantially light opaque resin.

The lenses 92 and the upper and lower light impermeable housing members can be molded from the same thermoplastic resin. The resin is preferably soft and flexible. Preferred resins include resins sold under the tradenames "DYNAFLEX" and "HANNAH THERMOPLASTIC ELASTOMER". These resins are all substantially transparent to light. To make the resins substantially opaque to light for use in the opaque portions of the upper housing member and in the lower housing member, color bodies, preferably light absorptive or reflective, are incorporated into the resin. Preferred additives to form the color bodies are pigments and polyethylene wax. Preferably, the resin includes from about 2 to about 30% by weight of such additives. The use of the same thermoplastic resin in both the lenses and the housing members provides a soft flexible front surface 68 for contacting the patient's skin, provides a smooth transition between the lenses and the surrounding portions of the upper housing member 300, and provides a high integrity seal between the lenses and upper housing member. As will be appreciated, the heat and pressure of the insert molding operation tends to melt the edges of the lenses allowing them to seal to the surface of the upper housing member. This type of bonding is not possible with dissimilar materials with varying melting points.

The formation of the lenses and housing members from the common intermediate thermoplastic resin advantageously provides a housing having substantially uniform properties. By way of example, the yield and tensile strengths of the lenses on the one hand and light opaque body on the other are preferably within about 10% of one another. The moduli of elasticity of the lenses and light opaque body are preferably within about 10% of one another. The coefficients of thermal expansion/contraction of the lenses and opaque body are preferably within about 10% of one another.

The detector and emitters are deposited on the leadframe and sealed by an encapsulant 332. The encapsulant is applied by suitable techniques to both the upper and lower surfaces of the substrate containing the detector and emitters to provide a hermetic seal against ambient substances, such as water vapor. The preferred encapsulant is sold under the tradename "LOCTITE".

Referring to FIG. 20, the traces 324 on the leadframe are contacted with the conductors 368 in the wire 312 to form a leadframe assembly and the leadframe assembly sandwiched between the upper and lower housing members. Light impermeable disks 340a,b can be included to further reduce noise in the detector. Sufficient heat is applied by a heat sealing apparatus to the upper and lower housing members to melt the lips surrounding the perimeter of each member together and form a seal surrounding the leadframe assembly. An advantage of heat sealing is that the over molding step is eliminated from the injection molding process. Over molding is an expensive process that requires high cost tooling and a molding machine. Unless the manufacturing facility has a molding machine in-house the sensor components must be shipped back to the molder for final assembly. Heat sealing the two parts together allows for lower cost assembly tooling and permits the manufacturer to complete the assembly in-house.

The assembled sensor is positioned in the cavity and attached to the backing material using a suitable adhesive, such as medical grade rubber-based adhesives.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. In a sensing device for measuring the oxygen content of a patient's bloodstream, the sensing device comprising:

a leadframe for operatively connecting at least one of (a) an emitter means for irradiating the patient's bloodstream and (b) a detector means for providing a signal in response to a radiation portion passing through the bloodstream to an oximeter processing and display unit, the leadframe having a first portion having a first thickness and a second portion having a second thickness with the first thickness being greater than the second thickness.

2. The sensing device of claim 1, wherein the first portion of the leadframe contacts at least one of the detector means and the emitter means.

3. The sensing device of claim 1, wherein the first thickness ranges from about 10 to about 20 mils.

4. The sensing device of claim 1, wherein the detector means and emitter means are at opposite ends of the leadframe and the second portion of the leadframe is located between the detector means and emitter means.

5. The sensing device of claim 1, wherein the second thickness ranges from about 5 to about 10 mils.

6. The sensing device of claim 1, wherein the leadframe comprises a first set of traces between the emitter means and detector means and a second set of traces extending from the emitter means to wire means for connecting the sensing device to an oximeter processing and display unit, the first portion including the second set of traces and the second portion including the first set of traces.

7. The sensing device of claim 1, further comprising a housing for containing the at least one of the emitter means and detector means, the housing including a substantially transparent lens adjacent to the at least one of the emitter means and detector means and a housing body enclosing the at least one of the emitter means and detector means, wherein the housing body and lens are composed of the same base thermoplastic material and have substantially the same degree of elasticity; wherein the lead frame includes a plurality of spaced-apart traces and the housing body includes a plurality of rib members, with one or more rib members being received between adjacent traces; and wherein the housing has upper and lower portions and the upper and lower portion each has a lip portion projecting outwardly from the corresponding one of the upper and lower portions, the lip portion of the upper portion being sealed to a lip portion on the lower portion to protect at least one of the emitter means and detector means from fluids in the terrestrial environment.

8. In a sensing device for measuring the oxygen content of a patient's bloodstream, the sensing device comprising:

a housing for containing at least one of (a) an emitter means to irradiating the patient's bloodstream and (b) a detector means for providing a signal in response to a radiation portion passing through the bloodstream, the housing including a substantially transparent lens adjacent to the at least one of the emitter means and detector means and a housing body enclosing the at least one of the emitter means and detector means, wherein the housing body and the lens are composed of the same base thermoplastic material that at least one of the melting point, yield tensile strength, ultimate tensile strength, modulus of elasticity, coefficient of thermal expansion, and durometer of the lens is within about 10% of a corresponding at least one of the melting point, yield tensile strength, ultimate tensile strength, modulus of elasticity, coefficient of thermal expansion, and durometer of the housing body, and wherein the lens is molded to the housing to provide a sealed and smooth transition therebetween.

9. The sensing device of claim 8, wherein the lens is substantially free of color bodies.

10. The sensing device of claim 8, wherein the housing body contains color bodies.

11. The sensing device of claim 8, wherein the housing body contains from about 2 to about 30% by weight color bodies.

12. The sensing device of claim 8, wherein thermoplastic resin forming the lens has substantially the same melting point as the thermoplastic resin forming the housing body.

13. The sensing device of claim 8, wherein the difference between the melting point of the thermoplastic resin forming the lens and melting point as the thermoplastic resin forming the housing body is no more than about 25° F.

14. The sensing device of claim 8, wherein the melting point of the thermoplastic resin forming the lens is at least about 75% and no more than about 125% of the melting point of the thermoplastic resin forming the housing body.

15. The sensing device of claim 8, wherein the housing body and lens have substantially the same degree of elasticity and has upper and lower portions with the upper and lower portion each having a lip portion projecting outwardly from the corresponding one of the upper and lower portions, the lip portion of the upper portion being sealed to a lip portion on the lower portion to protect at least one of the emitter means and detector means from fluids in the terrestrial environment, and further comprising a lead frame for operably connecting at least one of the emitter means and detector means to an oximeter processing and display unit, the lead frame having a first portion having a first thickness and a second portion having a second thickness with the first thickness being greater than the second thickness and wherein the lead frame includes a plurality of spaced-apart traces and the housing body includes a plurality of rib members, with one or more rib members being received between adjacent traces.

16. In a sensing device for measuring the oxygen content of a patient's bloodstream, the sensing device comprising:
a housing for containing at least one of (a) an emitter mean for irradiating the patient's bloodstream and (b) a detector means for providing a signal in response to a radiation portion passing through the bloodstream, the housing including a substantially transparent lens adjacent to the at least one of the emitter means and detector means and a housing body enclosing the at least one of the emitter means and detector means, and wherein the lens is molded to the housing to provide a sealed and smooth transition therebetween.

17. The sensing device of claim 16, wherein the lens is substantially free of color bodies.

18. The sensing device of claim 16, wherein lens and housing body are composed of the same base thermoplastic material.

19. The sensing device of claim 16, wherein the housing body contains from about 2 to about 30% by weight color bodies.

20. The sensing device of claim 16, wherein thermoplastic resin forming the lens has substantially the same melting point as the thermoplastic resin forming the housing body.

21. The sensing device of claim 16, wherein the difference between the melting point of the thermoplastic resin forming the lens and melting point as the thermoplastic resin forming the housing body is no more than about 25%.

22. The sensing device of claim 16, wherein the melting point of the thermoplastic resin forming the lens is at least about 75% and no more than about 125% of the melting point of the thermoplastic resin forming the housing body.

23. The sensing device of claim 16, wherein the housing body and lens are composed of the same base thermoplastic material and has upper and lower portions with the upper and lower portion each having a lip portion projecting outwardly from the corresponding one of the upper and lower portions, the lip portion of the upper portion being sealed to a lip portion on the lower portion to protect at least one of the emitter means and detector means from fluids in the terrestrial environment, and further comprising a lead frame for operatively connecting at least one of the emitter means and detector means to an oximeter processing and display unit, the lead frame having a first portion having a first thickness and a second portion having a second thickness with the first thickness being greater than the second thickness and wherein the lead frame includes a plurality of spaced-apart traces and the housing body includes a plurality of rib members, with one or more rib members being received between adjacent traces.

24. In a sensing device for measuring the oxygen content of a patient's bloodstream, the sensing device comprising:
a housing enclosing (a) at least one of an emitter means for irradiating the patient's bloodstream and a detector means for providing a signal in response to a radiation portion passing through the bloodstream and (b) a leadframe for operatively connecting the at least one of the emitter means and detector means with an oximeter processing and display unit, wherein the leadframe includes a plurality of bare, spaced-apart, conductive traces and the housing body includes a plurality of rib members, with one or more rib members being positioned between adjacent traces to align and electrically isolate the bare traces.

25. The sensing device of claim 24, wherein the thickness of the rib members is at least 25% of the distance between adjacent traces.

26. The sensing device of claim 24, wherein a first set of traces is located between the detector means and the emitter means and a second set of traces is located between the at least one of the detector means and emitter means and wire means for connecting the sensing device to the oximeter processing and display unit and a first set of rib members engages the first set of traces and a second set of rib members engages the second set of traces.

27. The sensing device of claim 24, wherein a first portion of a first rib member received between adjacent traces has a greater width than an adjacent portion of the first rib member, thereby defining a nub.

28. The sensing device of claim 27, wherein a second rib member is adjacent to the first rib member, the second rib member comprising a second portion having a width greater than an adjacent portion thereof and wherein the distance between the first portion of the first rib member and the second portion of the second rib member is less than the width of a trace received therebetween.

29. The sensing device of claim 24, wherein the lead frame has a first portion having a first thickness and a second portion having a second thickness with the first thickness being greater than the second thickness and the housing includes a housing body and lens, with the housing body and lens being composed of the same base thermoplastic material and having the same degree of elasticity and has upper and lower portions with the upper and lower portion each having a lip portion projecting outwardly from the corresponding one of the upper and lower portions, the lip portion of the upper portion being sealed to a lip portion on the lower portion to protect at least one of the emitter means and detector means from fluids in the terrestrial environment.

30. In a sensing device for measuring the oxygen content of a patient's bloodstream, the sensing device comprising:
a housing enclosing at least one of an emitter means for irradiating the patient's bloodstream and a detector means for providing a signal in response to a radiation portion passing through the bloodstream, wherein the housing has adjoined upper and lower portions, and wherein the upper portion and lower portion are heat-sealed together about their respective peripherals to form a lip portion projecting outwardly from the upper and lower portions, the lip portion protecting emitter means and detector means from fluids in the terrestrial environment.

31. The sensing device of claim 30, wherein at least one of the lip portions has a tongue or a groove to engage a groove or a tongue, respectively, on the other lip portion.

32. The sensing device of claim 30, wherein the upper and lower portions of the housing form a housing body and include a lens adjacent to at least one of the emitter means and detector means and wherein the housing body and lens are composed of the same base thermoplastic material and have the same degree of elasticity and further comprising a lead frame for operatively connecting at least one of the emitter means and detector means to an oximeter processing and display unit, the lead frame having a first portion having a first thickness and a second portion having a second thickness with the first being greater than the second thickness and the lead frame including a plurality of spaced-apart traces and the housing body including a plurality of rib members, with one or more rib members being received between adjacent traces.

33. A method for forming a leadframe for an oximeter sensing device, comprising:

cutting a leadframe body from a conductive sheet; and applying an etchant to a selected portion of the leadframe body to form a leadframe having different thicknesses.

34. The method of claim 33, wherein the applying step comprises:

applying a masking material to a second portion of the leadframe body other than the selected portion; and applying the etchant to the selected portion and the second portion.

35. The method of claim 33, wherein the applying step comprises:

applying the etchant only to the selected portion of the leadframe body.

36. The method of claim 33, wherein the applying step comprises:

etching the selected portion of the leadframe body for a first time period; and etching another portion of the leadframe for a second time period, wherein the first time period exceeds the second time period.

37. The method of claim 33, wherein the cutting step comprises cutting the leadframe from a conductive sheet using a cutting die having substantially the same size and shape as a cavity in an oximeter sensor housing for receiving a leadframe and further comprising:

forming a thermoplastic resin;

molding a first portion of the thermoplastic resin to form a light transparent lens for at least one of a detector and emitter;

mixing a second portion of the thermoplastic resin with a color body to form a substantially light opaque, thermoplastic resin;

molding the substantially light opaque, thermoplastic resin to form a housing body having upper and lower portions for enclosing a lead frame, the upper portion of the housing having a first lip projecting outwardly from the upper portion for engaging a second lip on the lower portion with the second lip projecting outwardly from the lower portion;

engaging the first lip with the second lip; and heating the upper and lower portions to above the melting point of the first and second lips to seal the upper portion and the lower portion.

38. A method for manufacturing an oximeter sensor, comprising:

cutting a conductive sheet to define a leadframe having a plurality of conductive traces using a cutting die having substantially the same size and shape as a cavity in an oximeter sensor housing for receiving the leadframe;

positioning the leadframe and plural traces into said cavity of the oximeter sensor housing.

39. The method of claim 38, wherein the distance between the edge of the cavity and the outer edge of the leadframe is no more than about 25 mils.

40. The method of claim 38, further comprising:

applying an etchant to a selected portion of the lead frame body to form a lead frame having different thicknesses;

forming a thermoplastic resin;

molding a first portion of the thermoplastic resin to form a light transparent lens for at least one of a detector and emitter;

mixing a second portion of the thermoplastic resin with a color body to form a substantially light opaque thermoplastic resin;

forming upper and lower portions of the housing for enclosing the lead frame, the upper portion of the housing having a first lip projecting outwardly from the upper portion for engaging a second lip on the lower portion with the second lip projecting outwardly from the lower portion;

engaging the first lip with the second lip; and heating only the first lip and second lip to above the melting point of the first and second lips to seal the upper portion to the lower portion.

41. A method for forming an oximeter sensing device, comprising:

forming a thermoplastic resin;

molding a first portion of the thermoplastic resin to form a light transparent lens for at least one of a detector and emitter;

mixing a second portion of the thermoplastic resin with a color body to form a substantially light opaque thermoplastic resin, said second portion being separate from the first portion; and molding the substantially light opaque thermoplastic resin to form a housing body for the oximeter sensing device; including:

positioning the light transparent lens for at least one of a detector and emitter in a mold for the housing body; and contacting the mold with the substantially light opaque thermoplastic resin, the substantially light opaque thermoplastic resin having a temperature at or above the melting temperature of the thermoplastic resin; and cooling the substantially light opaque thermoplastic resin to form the housing body, wherein the lens is molded to said housing body.

42. The method of claim 41, wherein the molding step comprises:

forming upper and lower portions of the housing for enclosing the lead frame, the upper portion of the housing having a first lip projecting outwardly from the upper portion for engaging a second lip on the lower portion with the second lip projecting outwardly from the lower portion;

engaging the first lip with the second lip; and heating the upper and lower portions to above the melting point of the first and second lips to seal the upper portion to the lower portion; and further comprising:

cutting the lead frame from a conductive sheet using a cutting die having substantially the same size and shape as a cavity in the housing for receiving the lead frame; and applying an etchant to a selected portion of the lead frame body to form a lead frame having different thicknesses.

43. A method for forming an oximeter sensing device, comprising:

forming upper and lower portions of a housing for enclosing a leadframe, the upper portion of the housing having a first lip projecting outwardly from the upper portion for engaging a second lip on the lower portion with the second lip projecting outwardly from the lower portion;

engaging the first lip with the second lip; and heating the first lip and second lip to above the melting point of the first and second lips to heat-seal the upper portion to the lower portion wherein said heating is restricted to said first lip and said second lip.

44. The method of claim 43 wherein the forming step comprises:

forming a thermoplastic resin;

molding a first portion of the thermoplastic resin to form a light transparent lens for at least one of a detector and emitter;

mixing a second portion of the thermoplastic resin with a color body to form a substantially light opaque thermoplastic resin; and molding the substantially light opaque thermoplastic resin to form a housing body for the oximeter sensing device; and further comprising:

cutting the lead frame from a conductive sheet using a cutting die having substantially the same size and shape as a cavity in an oximeter sensor housing for receiving the lead frame; and applying an etchant to a selected portion of the lead frame body to form a lead frame having different thicknesses.

\* \* \* \* \*

UNITED STATES PATENT AND TRADEMARK OFFICE
CERTIFICATE OF CORRECTION

PATENT NO.    : 5,913,819
DATED         : June 22, 1999
INVENTOR(S)  : TAYLOR et al.

It is certified that error appears in the above-identified patent and that said Letters Patent is hereby corrected as shown below:

At Column 12, line 25, delete the word "to" and insert --for-- therefor.
At Column 12, line 33, after the word "material", insert the word --so-- therefor.

Signed and Sealed this

Fourteenth Day of December, 1999

Attest:

Q. TODD DICKINSON

*Attesting Officer*      *Acting Commissioner of Patents and Trademarks*